United States Patent
Gogolides et al.

(10) Patent No.: US 7,326,510 B2
(45) Date of Patent: Feb. 5, 2008

(54) POLYCARBOCYCLIC DERIVATIVES FOR MODIFICATION OF RESIST, OPTICAL AND ETCH RESISTANCE PROPERTIES

(76) Inventors: Evangelos Gogolides, 32 Agias Zonis Street, Kipseli, Athens (GR) 11361; Panagiotis Argitis, 44 Pavlou Bakogianni Street, Mellaala, Attiki (GR); Elias Andrea Couladouros, Chemical Laboratories, Agricultural University of Athens, Iera Odos 75, Athens (GR) 11855; Veroniki Petrou Vidali, Institute of Physical Chemistry, NCSR Demokritos, Terma Patriarhu Grigiriu Street, PO Box 60228, Aghia Paraskevi (GR); Maria Vasilopoulou, 17 Digeni Street, Aghia Paraskevi, Attiki (GR) 15341; George Cordoyiannis, 2 Istrou Street, Athens, Athens (GR) 11142

( * ) Notice: Subject to any disclaimer, the term of this patent is extended or adjusted under 35 U.S.C. 154(b) by 190 days.

(21) Appl. No.: 10/494,547

(22) PCT Filed: Oct. 31, 2002

(86) PCT No.: PCT/EP02/12284

§ 371 (c)(1),
(2), (4) Date: Apr. 30, 2004

(87) PCT Pub. No.: WO03/038523

PCT Pub. Date: May 8, 2003

(65) Prior Publication Data

US 2005/0026068 A1 Feb. 3, 2005

(30) Foreign Application Priority Data

Nov. 1, 2001 (GR) .............................. 20010100506

(51) Int. Cl.
G03F 7/004 (2006.01)

(52) U.S. Cl. ..................... 430/270.1; 430/905; 430/910

(58) Field of Classification Search ............. 430/270.1, 430/905, 910
See application file for complete search history.

(56) References Cited

U.S. PATENT DOCUMENTS

| | | | |
|---|---|---|---|
| 3,807,999 A | 4/1974 | DeSchrijver et al. | 96/27 F |
| 5,059,512 A | 10/1991 | Babich et al. | 430/280 |
| 5,098,816 A | 3/1992 | Babich et al. | 430/325 |
| 5,110,711 A | 5/1992 | Babich et al. | 430/296 |
| 5,695,910 A | 12/1997 | Urano et al. | 430/270.1 |
| 5,731,125 A | 3/1998 | Yamachika et al. | 430/270.1 |
| 5,736,301 A | 4/1998 | Fahey et al. | 430/325 |
| 6,037,107 A | 3/2000 | Thackeray et al. | 430/326 |
| 6,045,968 A | 4/2000 | Ushirogouchi et al. | 430/270.1 |
| 6,156,477 A | 12/2000 | Motomi et al. | 430/270.1 |
| 6,238,842 B1 | 5/2001 | Sato et al. | 430/281.1 |

FOREIGN PATENT DOCUMENTS

| | | |
|---|---|---|
| DE | 100 09 183 | 2/2000 |
| DE | 100 09 183 A | 9/2000 |
| EP | 0 726 500 A | 8/1996 |
| EP | 0 834 770 A | 4/1998 |
| EP | 1 126 320 | 1/2001 |
| EP | 1 123 320 A | 8/2001 |

OTHER PUBLICATIONS

Dabbagh et al. "Model Study of FT-IR of the Interaction of Select Chocolate Dissoluation Inhibitors with Poly(norbornene-alt-maleic anhydride) and its derivatives," Proc. SPIE—The Int'l Optical Eng'g 3678(1):86-93 (Mar. 17, 1999).
Castellan, Alain et al, Studies on Aromatic Trichromophore Systems Incorporating Anthracene Moieties. Part 1. Synthesis, Fluorescence and Photoreactivity, 1993, pp. 953-961, J. Chem. Soc. Perkin Trans. 2.
Ishikawa, Junichi et al, Silver Ion Selective Fluroionophores Based on Athracene-Linked Polythiazaalkane or Polythiaalkane Derivatives, 1999, pp. 1913-1921, J. Org. Chem. 64.
Powell, Michael F., Facile Aryl Ether Hydrolysis: Kinetics and Mechanism of 9-Anthryl Ether Clevage in Aqueous Solution, 1987, pp. 56-61, J. Org. Chem. 52.
Dabbagh, G., et al. A Model Study by FT-IR of the Interaction of Select Cholate Dissolution Inhibitors with Poly(Norbornene-alt-Maleic Anhydride) and its Derivatives, Mar. 1999, pp. 86-93, SPIE vol. 3678.
Conley, Willard, et al., Negative i-line photoresist for 0.5 µm and beyond, Nov./Dec. 1992, pp. 2570-2575, J. Vac. Sci. Technol. B 10 (6).
Argitis, P. et al., Etch Resistance Enhancement and Absorbance Optimization with Polyaromatic Compounds for the Designof 193 nm Photoresists, 1998, pp. 355-358, Elsevier Microelectronic Engineering 41/42.
Pederson, Lester A., Structural Composition of Polymers Relative to Their Plasma Etch Characteristics, Deep U.V. Lithography, vol. 129, No. 1, Jan. 1982, pp. 205-208.
Naito, Takuya, et al. Highly Transparent Chemically Amplified ArF Excimer Laser Resists by Absorption Band Shift for 193 nm Wavelength, Dec. 1994, pp. 7028-7032, Jpn. J. Appl. Shys., vol. 33, Part 1, No. 12B.
Kunz, R.R., et al., Limits to Etch Resistance for 193-nm Single-Layer Resists, Jun. 1996, pp. 365-376, SPIE vol. 2724.
Gokan, H., et al., Dry Etch Resistance of Organic Materials, Jan. 1983, pp. 143-146, Kinetics of Changes, vol. 130, No. 1.
Tepermeister, I., et al., X-ray photoelectron spectroscopy study of polymer surface reactions in F2 and O2 gases and plasmas, Sep./Oct. 1992, pp. 3149-3157, J. Vac. Sci. Technol. A 10(5).

*Primary Examiner*—John S. Chu
(74) *Attorney, Agent, or Firm*—Mathews, Shepherd, McKay & Bruneau, P.A.

(57) ABSTRACT

Mixed carbocycle derivatives containing at least two carbocycles per molecule from the group of anthracenes, adamantanes and steroids with functionalized carbon chains are synthesized and used as modifiers of resist properties and especially etch resistance enhancement and absorption characteristics. These derivatives are characterized by formulas I-V, where A and R may be an anthryl- and/or an adamantyl- and/or a steroid moiety. Methods for the preparation of the above compounds are disclosed.

6 Claims, No Drawings

POLYCARBOCYCLIC DERIVATIVES FOR MODIFICATION OF RESIST, OPTICAL AND ETCH RESISTANCE PROPERTIES

FIELD OF THE INVENTION

This invention relates to mixed carbocycle derivatives containing at least two carbocycles per molecule from the group of anthracenes, adamantanes and steroids with functionalized carbon chains, to their preparation and to their use as modifiers of resist properties.

BACKGROUND OF THE INVENTION

Photoresists capable of 0.1-0.2 μm resolution in production, using optical exposure, have already entered the market, whereas research efforts for materials and processes targeting at even lower dimensions are being explored. The exposure wavelength defines to a great extent the ultimate photoresist resolution properties. Currently, 248 nm and 193 nm exposures are mostly used for the production of 0.1-0.2 μm features and research efforts are underway for even smaller dimensions, using 157 nm and 13 nm electromagnetic radiation.

Photoresists used in modem lithographic applications should combine a number of properties in order to be suitable for high-resolution patterning. Among them the appropriate absorbance at the exposure wavelength and the resistance to the plasmas used during the pattern transfer step are especially important.

As the lateral structure dimensions shrink, thin photoresist films, usually below half micron, are used to keep aspect ratios low and thus to facilitate lithographic processes. Consequently, the importance of the film etch resistance for effective pattern transfer increases. Traditionally, the etch resistance properties of the resist material were obtained using phenolic polymers. This was the case in 436 nm, 365 nm and 248 nm exposure. Since aromatic polymers—novolacs as well as poly(hydroxystyrene) based resins—are highly absorbant to 193 nm light, single layer photoresist systems for 193 nm lithography are usually based on aliphatic polymers which show low absorbance, at this wavelength. However, aliphatic polymers have roughly twice as high etching rates than aromatic ones, classically used in previous generation photoresist systems (L. A Pederson, J. Electrochem. Soc., 129 (1), 205-8 (1982)), despite the initial reactivity of aromatic polymers in the plasma environment:

According to the accepted polymer etching mechanism, halogen atoms add to the double bonds first, as opposed to subtraction of hydrogen atoms from the saturated carbon bonds, and the resulting halogenated compound is less reactive than the product of abstraction (Tepermeister and H. H. Sawin, J. Vac. Sci. Technol. A 10 (5), 3149-57 (1992)). The etching rate was found to be inversely proportional to the [Carbon-Oxygen] atom content of the polymer (H. Gokan, S. Esho, Y. Ohnishi, J. Electrochem. Soc., 130 (1), 143-6 (1983)), and an empirical parameter referred to as *The Ohnishi Parameter, O=(Total Number of Carbon atoms/ (Carbon-Oxygen atoms)* has been defined. The smaller the Ohnishi parameter (O) the higher the etch resistance. For example poly(hydroxystyrene)—a very etch resistant polymer—has O=2.43, while PMMA—a non-etch resistant polymer—has O=5. Etch resistance was also characterized with the amount of Carbon atoms present in a ring structure, and another improved empirical parameter referred to as *The Ring Parameter R=(Mass of Carbon atoms in Rings)/(Total Mass of Polymer)* was defined recently. The higher the value of R (and closer to unity), the higher the etch resistance of the polymer. See for example (R. R Kunz, S. C. Palmateer, A. R. Forte, R. D. Allen, G. M. Wallraff, R. A. DiPietro, D. C. Hofer, "Limits to etch resistance for 193-nm Single-Layer Resists", Proceedings SPIE, Advances in Resist Technology and Processing, Vol. 2724, p.365-76, 1996). For example poly(hydroxystyrene)—a very etch resistant polymer—has R=0.6, while PMMA—a non-etch resistant polymer—has R=0. Notice that high etch resistance is characterized by high R-values (close to unity) and small O-values. In any case, high carbon and double bond content, high carbon content in ring structures, as well as low oxygen/nitrogen content are desirable for better plasma resistance. Thus, to address the etch resistance problem in 193 nm, polymeric materials containing cycloaliphatic moieties, either attached to the polymer chain or as separate components, were used by most resist companies and universities in an effort to obtain carbon-carbon bonding groups similar to the ones of the benzyl ring. Nevertheless, as it was first suggested (T. Naito, K. Asakawa, N. Shida, T. Ushirogouchi and M. Nakase, "Highly Transparent Chemically Amplified ArF Excimer Laser Resists by Absorption Band Shift for 193 nm Wavelength" Jpn. J. Appl. Phys., 33, 7028-32 (1994)), another route in order to enhance the etch resistance of these aliphatic polymers, while keeping acceptable absorbance, can be provided by polyaromatic compounds such as naphthalene, anthracene and their derivatives. These are characterized by a significant red shift of the absorption band, which in simple aromatic compounds is centered around 193 nm and thus, they are significantly more transparent at this wavelength. It has been shown by some of the inventors and collaborators (P. Argitis, M. Vasilopoulou, E. Gogolidēs et al "Etch resistance enhancement", Microelectron. Eng. 1998) that anthracene loading is effective in increasing the etch-resistance, i.e. reduction of the etching rate of the PMMA by more than 30% is obtained at loadings slightly higher than 5%. In comparison, addition of more than 10% w/w is required for the same etch resistance increase in the case of adamantane (cycloaliphatic) derivatives.

Similar challenges, i.e. to enhance etch resistance with polymers or additives that have suitable absorbance at the exposure wavelength, are encountered in other wavelengths, as well. For instance, in EUV (13 nm), one of the most probable spectral areas to be used in the next generation lithography, it has been recently shown, on the basis of absorbance considerations, that thickness of 0.15-0.25 μm could be tolerated for most materials. Since film thickness in this range is considered rather low compared to the thickness used so far, the highest possible etch resistance of the resist materials is desired. The increase of the resist etch resistance is also desirable even at longer wavelengths e.g. 248 nm or 436 nm, since it allows the use of thinner resist films and thus smaller aspect ratios for high resolution patterning. Analogous arguments can be also provided for 157 nm e-beam and X-ray lithographies.

The anthracene derivatives, mentioned above as possible etch resistance additives, have been also used in photoresist formulations to control absorbance and/or photochemical properties at certain wavelengths. Thus, 9-anthracene methanol has been used as near UV photosensitizer by a number of investigators (W. Conley and J. Gelorme, "Negative i-line resist for 0.5 μm and beyond", J. Vac. Sci. Technol. B, 10 (1992) and U.S. Pat. Nos. 5,110,711, 5,098, 816 and 5059512). On the other hand, other patents (see for example U.S. Pat. No. 5,731,125) have been granted for the use of anthracene derivatives, e.g. anthracene-9-carboxy-ethyl and 9-anthracene-methanol, as additives to control resist absorbance for chemically amplified resist compositions. Anthracene derivatives as deep UV absorbers have been also used in resist compositions described in U.S. Pat. No. 5,695,910. The absorbing properties of anthracene derivatives are also used in a number of recent patents (see for example U.S. Pat. No. 5,736,301) where anthracenes, incorporated in a polymer backbone or as additives are part of antireflective coatings placed under photoresist films. In this last case, where anthracene derivatives are used in the composition of antireflective coatings, special care is taken for the film to have optimum etch resistance. Too high etch resistance of the antreflective coating is undesirable, since it causes problems to the proper film removal after pattern transfer.

Other etch resistance additives, and resist compositions incorporating same are described in G. Dabbagh et al, Proceedings of the SPIE—The International Society for Optical Engineering; 3678 (1999) 86; European Patent Application EP-A-1126320; U.S. Patents U.S. Pat. No. 6,238,842 and U.S. Pat. No. 6,156,477; and German Patent Application DE-A-10009183, the contents of all of which are hereby incorporated by reference.

In general, the use of additives to improve certain properties in photoresist compositions is a versatile method, since it allows easy preparation of different material formulations, without requiring complicated polymer synthesis or chemical modification procedures. Nevertheless, restrictions are posed by the need to fulfill a number of physicochemical requirements defined by the lithographic process:

First, the additives must be compatible with the rest of the resist components to avoid any phase separation phenomena that can lead to film composition and property inhomogeneities.

Second, the additives should withstand the lithographic processing steps without decomposition, sublimation or process induced phase separation phenomena.

Finally, they should not modify substantially the resist chemical and physical properties leading to deterioration of the lithographic performance.

SUMMARY OF THE INVENTION

The invention provides photoresist property modifiers characterized by the presence of at least two polycyclic moieties per molecule, preferably where at least one of them is an anthracene derivative. The general formulae of these polycarbocydes are the following:

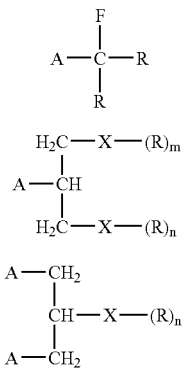

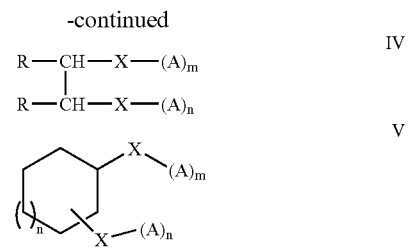

In the above formulae I-V:
n or m is an integer of 1 to 5,
F may be a hydrogen atom or from the group of —OH or —NH or —COOH or alkyl or alkoxy and X represents a linker from the group of —$CH_2$— or —O— or —$CH_2NH$— or —$CH_2O$— or —CO— or —NH— or —CONH— or —COO— or alkyl or —OCOO— or —OCONH— or oxygenated aliphatic chain or carbonylated aliphatic chain or carbocyclic, polysubstituted aliphatic chain or carbocyclic with functional groups F.

A represents an anthracene or adamantane or steroid moiety of the following structures:

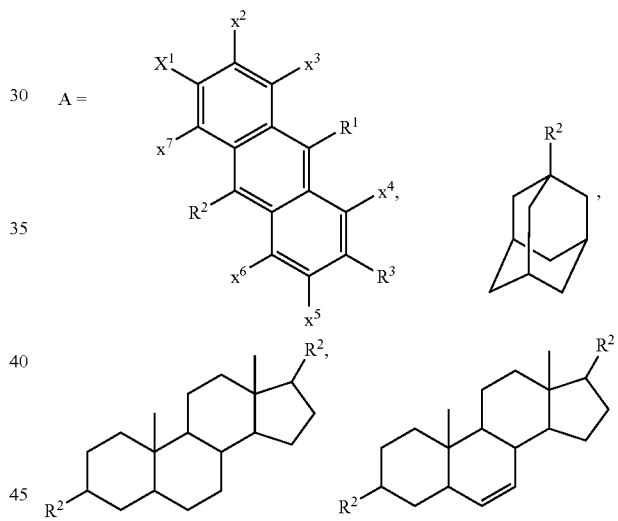

$R^1$ may be a hydrogen atom or alkyl or alkoxy or —$(CH_2)_v$—NHCO—$R^4$, in which v is an integer of 0 to 5 and $R^4$ represents a hydrogen atom, alkyl or alkoxy;
$R^2$ represents a linker such as —$CH_2$— or —O— or —$CH_2NH$— or —$CH_2O$— or —CO— or —NH— or —CONH— or —COO— or alkyl or —OCOO— or —OCONH— and it is not connected to $R^1$ by any chain;
$R^3$ includes functionalities such as hydrogen atom or a halogen or an alkyl or alkoxy group or an amino-derivative or a nitro group;
$X^1$ to $X^7$ may be the same as or different from one another and each thereof represents a hydrogen atom or an alkyl group or a halogen or a nitro group;
R stands for a hydrogen atom or an alkyl group or an additional moiety of the type A, F or X represented above.

In all the above descriptions, alkyl group includes for example methyl-, ethyl-, n-propyl-, isopropyl-, n-butyl-, isobutyl-, sec-butyl-, t-butyl-, n-pentyl-, n-hexyl-, n-octyl-, n-dodecyl-groups and the like. An alkoxy group includes for example methoxy-, ethoxy-, propoxy-, butoxy-, methoxymethylenoxy-, methoxyethylenoxy-group and the like. It should be noticed that none of the linkers represents any kind of polymeric chain.

The invention provides novel resist property modifiers characterized by the presence of at least two polycarbocydic moieties in their molecule, where at least one of them is an anthracene derivative. In particular, etch resistance enhancement additives characterized by the presence of polycydic moieties in their molecule. Molecules that contain two anthracene moieties or an anthracene and a second polycarbocycle, such as adamantane, norbornane or steroid, are especially useful for etch resistance enhancement. Furthermore, the polycarbocyclic additives containing at least one anthracene derivative provide suitable absorption properties to photoresists.

DETAILED DESCRIPTION OF THE PREFERRED EMBODIMENTS

The design, synthesis and use of molecules containing polycarbocycles as additives for photoresist property modification is described in detail below.

Many novel di- and poly-anthryl derivatives were synthesized aiming, at the improvement of the physicochemical properties and the etch resistance enhancement capability and their effectiveness was compared to that of known and commercially available mono-, di- and poly-anthryl derivatives. Some representative examples are shown in Tables 5-9.

It has been reported (U.S. Pat. No. 3,807,999) that anthryl derivatives with similar architecture to ours, yield products of intramolecular 4+2 (Diels-Alder) and 4+4 reactions when are exposed at 365 nm light, process that is reversed with exposure at 254 nm (scheme 7, page 23). We postulate that the same processes might occur under the extreme UV or temperature conditions during the etching process. In this case, it is anticipated that a molecule containing flat unsaturated groups will be transformed to a more condensed saturated carbon framework with dramatic effect on etch resistance.

The fact that other polycarbocycles, such as adamantane and steroids, provide also good etch resistance enhancement prompted us to synthesize various mixed derivatives of an anthryl moiety attached to these groups, as well. The physicochemical properties of some representative compounds are shown in Tables 4-8.

The synthesis of the compounds and their use as additives in resist formulations are presented below. The following steps are described:
a) the application of suitable synthetic routes or the development of new ones for the simple and efficient synthesis of precursors with suitable functional groups,
b) the combination of two or more additives in one molecule, using the above tested functional groups as linkage,
c) the testing of the physicochemical properties of the synthesized compounds including sublimation temperature and absorption characteristics and
d) the use of the synthesized compounds as photoresist etch resistance enhancement additives.

1. Detailed Description of the Synthetic Strategies Followed for the Preparation of the Newly-Synthesized Etch-Resistance Additives.

All the novel anthryl derivatives were prepared starting from commercially or synthetically available mono-anthryl derivatives. Consequently, several reported synthetic methods had to be modified or totally bypassed with new ones, in order to achieve efficient synthetic routes to the target molecules.

The following methods have been used for the preparation of the above anthracene derivatives:

Method 1

The method is illustrated in Scheme 1. Addition of the anion of anthracene, (A)—derived from 9-bromoahthracene (A) and 1 equivalent of n-butyllithium—to aldehydes, ketones, epoxides, epichloridrine, esters and the like for the formation of mono- or di-anthryl derivatives. Further derivatization of the above prepared alcohols eg 3 with several linkers to form di- or tri-anthryl derivatives, such as 4 and 5 or mixed anthracene derivatives with adamantane and steroids, such as 6 or 7.

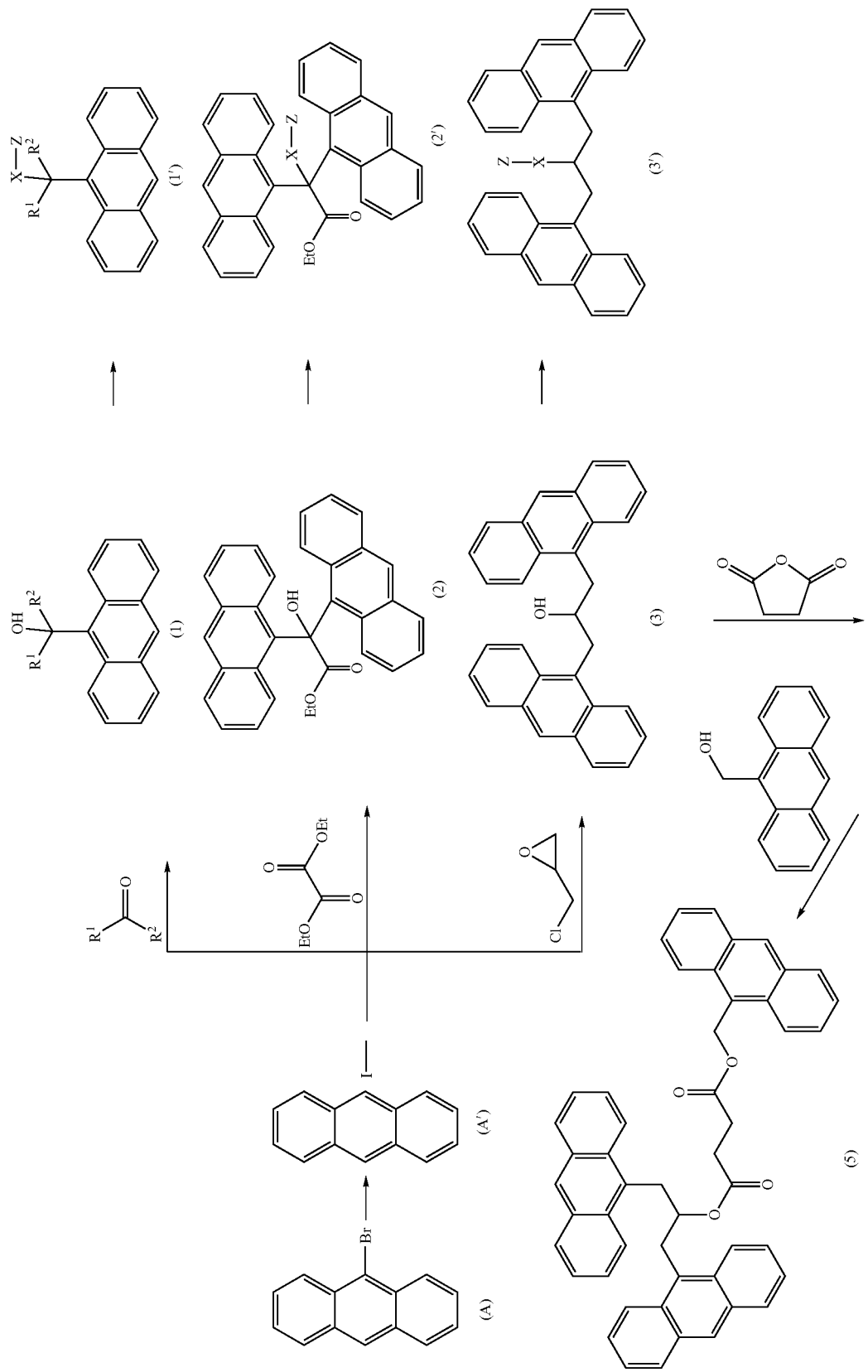

-continued
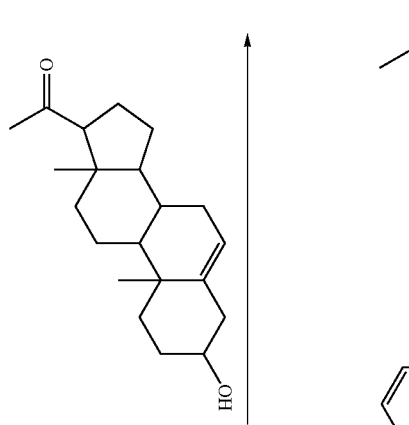
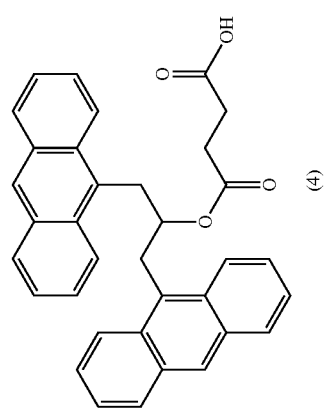
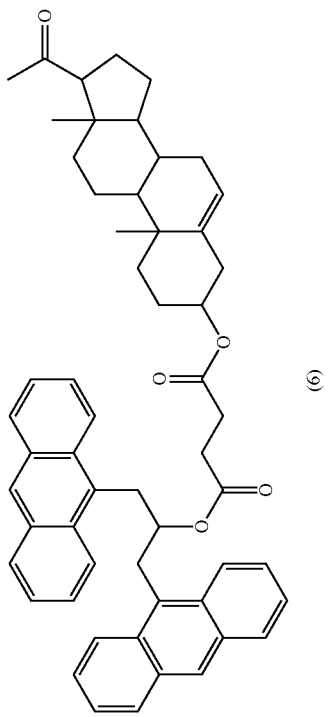
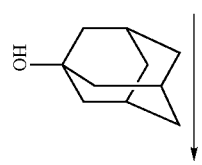
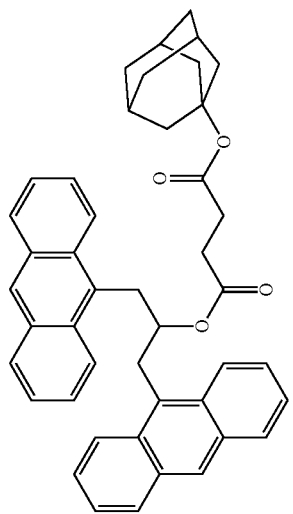
$R^1, R^2$ = H—, alkyl-, cycloalkyl-, hydroxyalkyl-, anthryl-, adamantyl-, steriod moiety e.t.c.
X = —O—, —O—(CH$_2$)$_n$—, —O—(CH$_2$)$_n$—O—(CH$_2$)$_n$—, —O—CO—(CH$_2$)$_n$—, —O—(CH$_2$)$_n$—CONH—(CH$_2$)$_n$—, —O—(CH$_2$)$_n$—COO— e.t.c.
—O—(CH$_2$)$_n$—NH—(CH$_2$)$_n$—,
Z = —H, 9-anthryl-, adamantyl-, steriod moiety, cycloalkyl-, e.t.c.
n = 1, 2, 3 . . .

Method 2

The method is illustrated in Scheme 2. Reaction of 9-anthrone (B) with diols and further derivatization of the resulted alcohols using some of the linkers, described previously, to form mono-, di-, poly- and mixed anthryl derivatives of the general type 8, 9, 10 and 11:

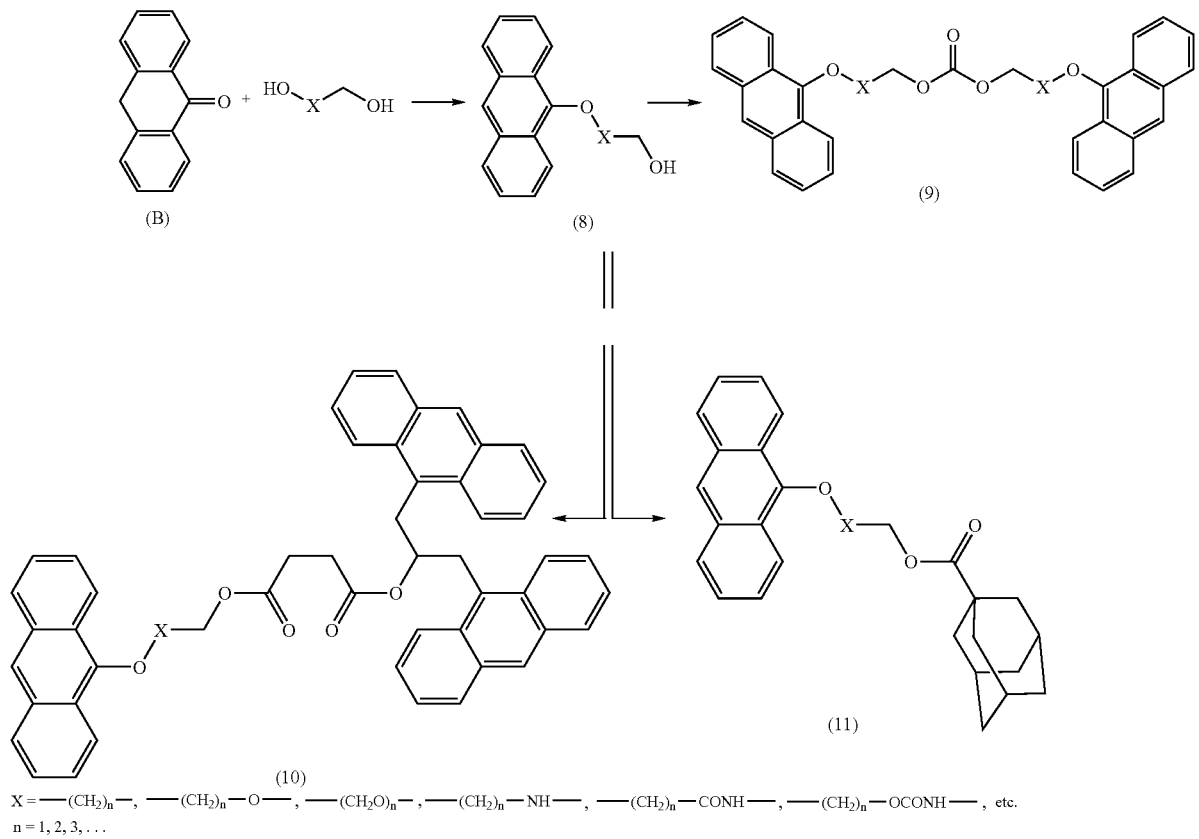

Method 3

The method is illustrated in Scheme 3. Derivatization of 9-anthracene methanol (C) with some of the above mentioned linkers, via esterification or etherificaton to form mono-, poly- or mixed derivatives of the general types 12-15.

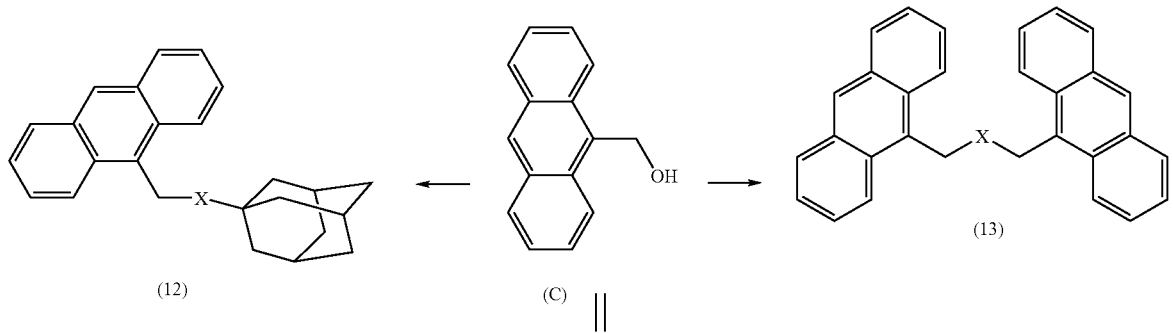

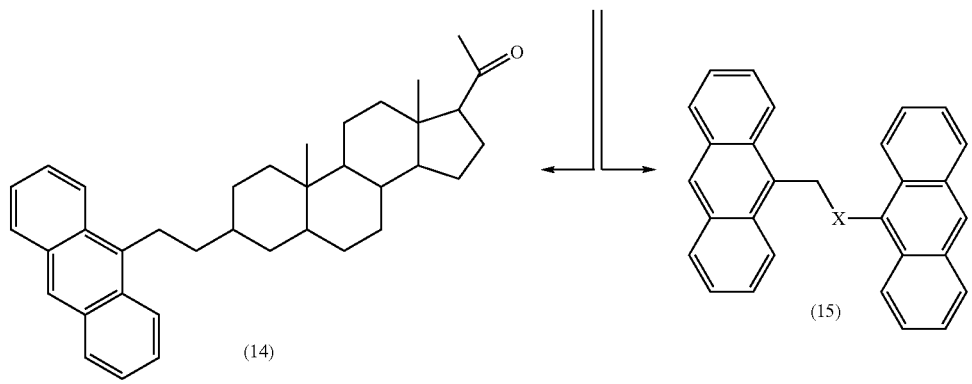

$X = -O-, -O-(CH_2)_n-, -O-(CH_2O)_n-O-, -O-CO-O-, -O-CO-, -O-(CH_2)_n-CO-O-,$
$-O-CO-(CH_2)_n-O-, -O-CO-(CH_2)_n-CO-O-, -O-(CH_2)_n-CONH-(CH_2)_n-O,$ etc.
$n = 1, 2, 3, \ldots$

Method 4

The method is illustrated in Scheme 4. Preparation of 9-aminomethyl derivatives from 9-chloromethyl anthracene (D) and primary mono-, di- or tri-amines with or without a linker, to form compounds of the general types 16-18.

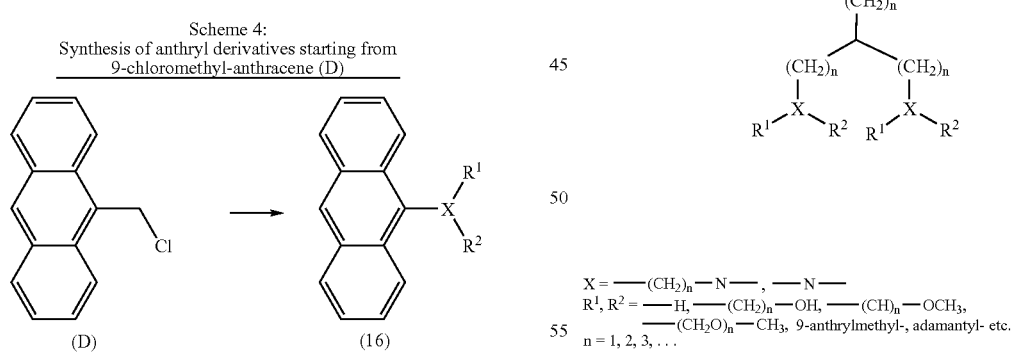

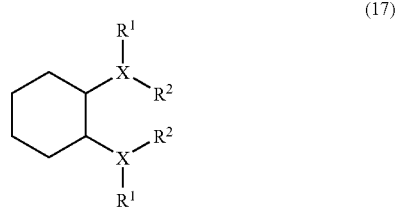

$X = -(CH_2)_n-N-, -N-$
$R^1, R^2 = -H, -(CH_2)_n-OH, -(CH)_n-OCH_3,$
$-(CH_2O)_n-CH_3,$ 9-anthrylmethyl-, adamantyl- etc.
$n = 1, 2, 3, \ldots$

Method 5

The method is illustrated in Scheme 5. Use of diol (20) prepared from 9-anthracarbaldehyde (E) (J. Ishikawa, H. Sakamoto, S. Nakao, H. Wad, *J. Ogr. Chem.* 1999, 64, 1913-1921), for the formation of mixed or poly-anthryl derivatives, of the general form 21 and 22, with or without the above mentioned linkers.

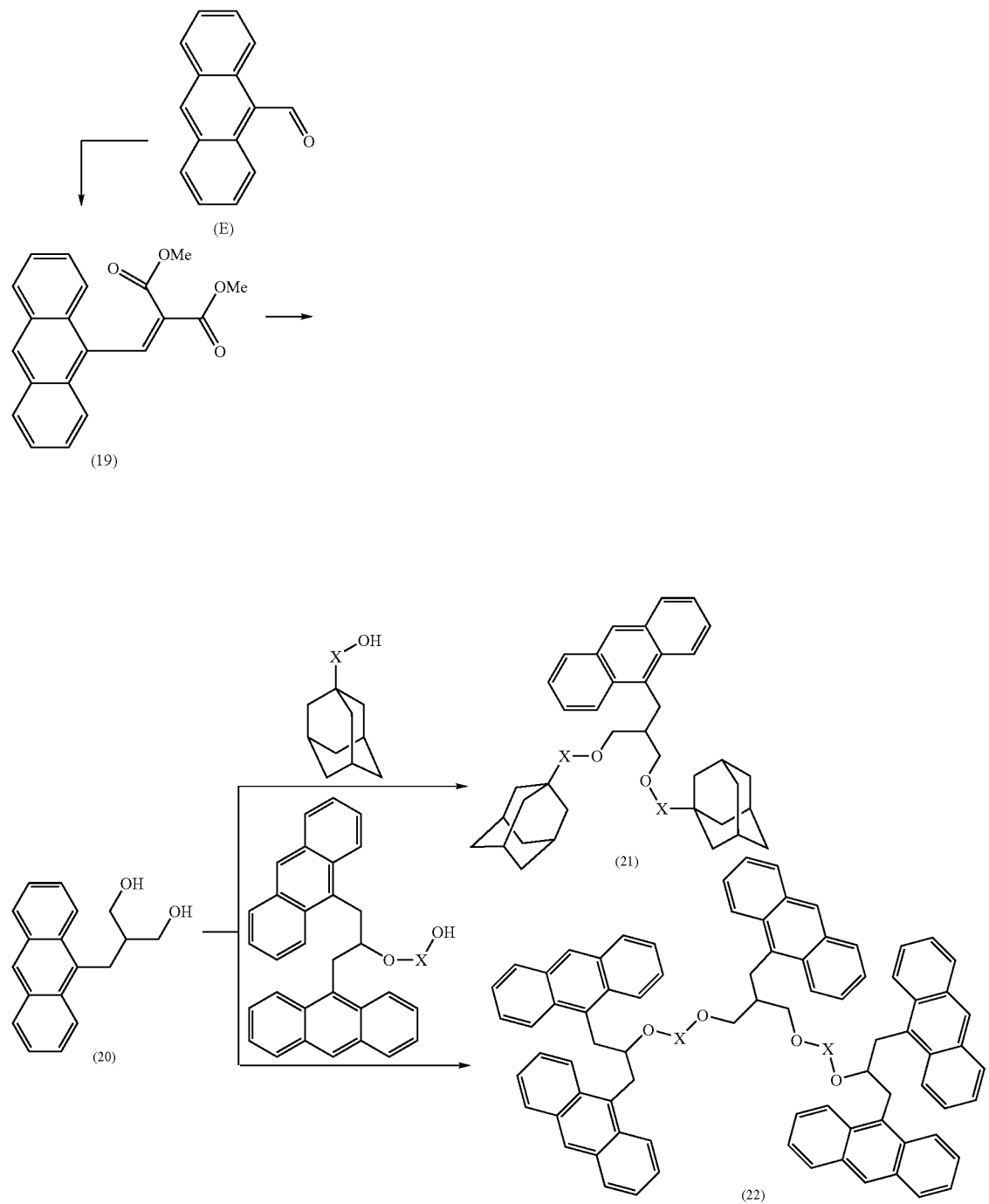
Scheme 5: Synthesis of anthryl derivatives starting from 9-anthracarbaldehyde (E)
X = —(CH$_2$)$_n$—, —(CH$_2$)$_n$—O—(CH$_2$)$_n$—, —CO—, —CO—(CH$_2$)$_n$—, —(CH$_2$)$_n$—CO—(CH$_2$)$_n$—, —(CH$_2$)$_n$—CONH—(CH$_2$)$_n$—, —CO—(CH$_2$)$_n$—CO—, —(CH$_2$)$_n$—NH—(CH$_2$)$_n$—, etc.
n = 1, 2, 3, …

Method 6
The method is illustrated in Scheme 6. Use of the chloride of 9-anthracene carboxylic acid (F), 23, for the preparation of mono-, poly-or mixed amido- or ester derivatives 24-26, with or without a linker.
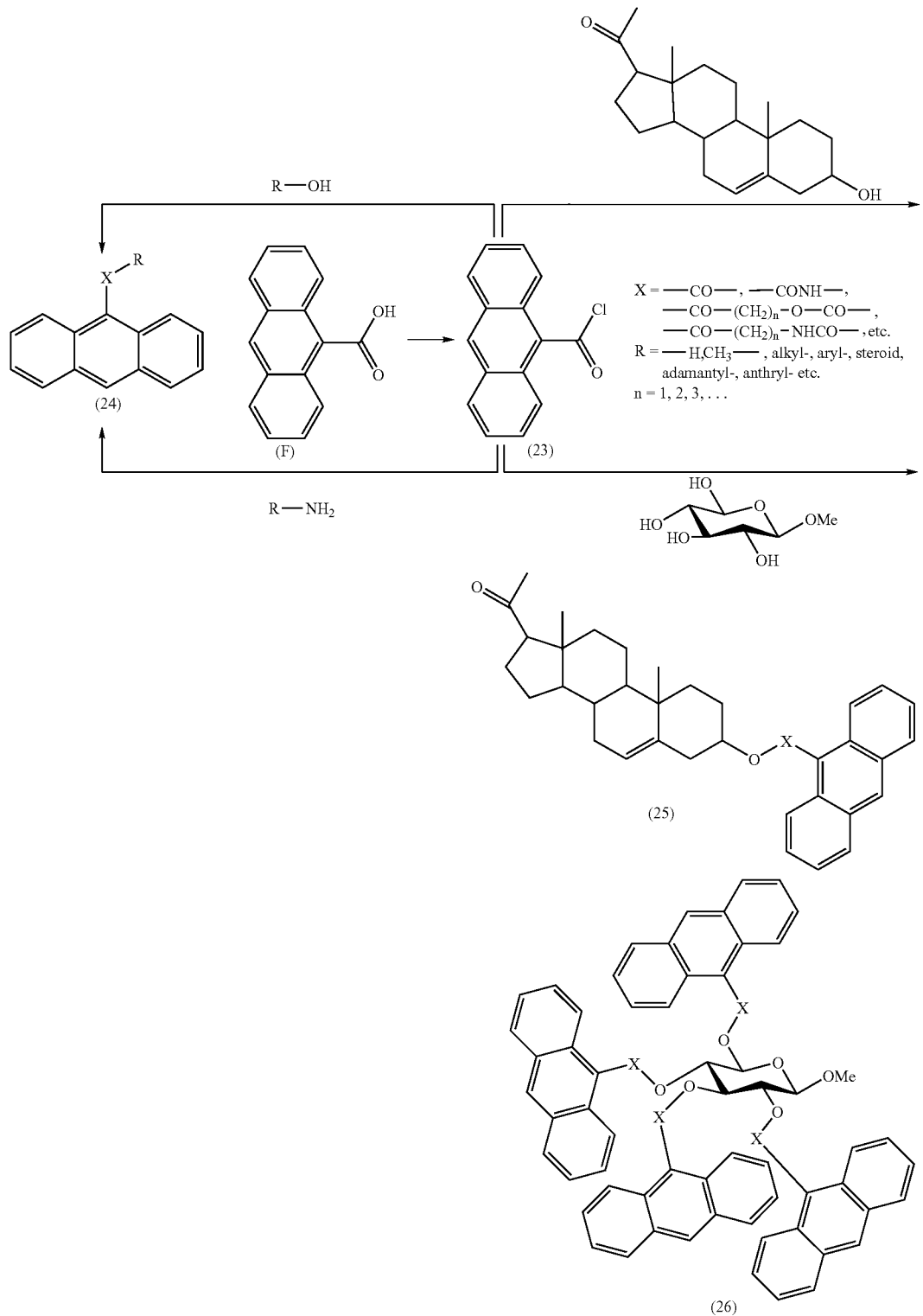

2. SYNTHESIS EXAMPLES

An illustrative example of the use of 9-bromoanthracene (A) for the synthesis of poly- and mixed anthryl derivatives is:

1,3-Di-(9-anthryl)-2-propyl 9-anthrylmethyl Succinate (5):

To a mixture of 1,3-di-(9-anthryl2-propyl hydrogen succinate (4) (103.3 mgr, 0.20 mmoles) prepared from 9-bromoanthracene (A. Castellan, L. Kessab, S. Grelier, A. Nourmamode, M. Cotrait, P. Marsau, *J. Chem. Soc. Perkin Trans. 2*, 1993, 953-961) (scheme 1), and 9-anthracene methanol (60.7 mgr, 0.29 mmoles), in dry dichloromethane (0.2 ml) a catalytic amount of 4-dimethylaminopyridine (4-DMAP) and 1-(3-dimethylaminopropyl)-3-ethylcarbodiimide hydrochloride (EDC.HCl) (42.48 mgr, 0.222 mmoles) was added, at ice bath temperature. The reaction mixture was stirred overnight under argon, at room temperature and then it was partitioned between water and ethyl acetate. The aqueous phase was washed with ethyl acetate twice and the combined organic extracts were washed with saturated ammonium chloride, water, brine, dried over sodium sulfate and concentrated in vacuo. The crude mixture was subjected to flash chromatography to afford 99.4 mgr (70%) of 1,3-di-(9-anthryl)-2-propyl 9-anthrylmethyl succinate which was further purified by recrystallization from dichloromethane (yellow crystals). $^1$H NMR (250 MHz, CDCl$_3$): δ 8.35 (5H, m), 8.00 (10H, d), 7.50-7.10 (12H, m), 6.10 (2H, s), 5.70 (1H, m), 4.10 (2H, dd), 3.65 (2H, dd), 2.10 (4H, t); $^{13}$C NMR (62.5 MHz, CDCl$_3$): δ 131.54, 131.15, 130.38, 129.62, 128.85, 126.92, 125.38, 124.62, 123.85, 63.85, 31.54, 30.38, 29.23, 28.46 ppm; FTIR 3050.0, 2920.0, 1723.9, 1158.7, 891.3, 731.0 cm$^{-1}$.

An illustrative example of the use of 9-anthrone (B) for the preparation of di-9-anthryl ethers is:

Di-2-(9-anthryloxy)-ethyl carbonate (9, X=—CH$_2$—):

To a stirred solution of 9-(2-hydroxyethoxy)anthracene (8, X=—CH$_2$—) (700 mgr, 3.27 mmoles), prepared according to Powell (M. F. Powell, *J. Org. Chem.* 1987, 52, 56-61) (scheme 2), in dry THF (0.4 ml), 1,1-carbonyldiimidazole (CDI) (177 mgr, 1.09 mmoles) was added and the reaction mixture was refluxed for 24 h. After cooling at room temperature and removal of the solvent in vacuo, the residue was subjected to flash chromatorapy and recrystallization from hexane-ethyl acetate to yield 334.9 mgr (61.1%) of pure di-2-(9-anthrytoxy)—ethyl carbonate. $^1$H NMR (250 MHz, CDCl$_3$): δ 8.40 (4H, d), 8.25 (2H, s), 8.00 (4H, d), 7.60-7.30 (8, m), 4.75 (4H, t), 4.50 (4H, t); $^{13}$C NMR (62.5 MHz, CDCl$_3$): δ 132.5, 128.5, 125.5, 124.5, 123.0, 122.0, 73.0, 67.0 ppm; FTIR 3050.0, 2900.0, 1744.8, 1338.1, 1268.3, 1241.0, 1090.8, 732.4 cm$^{-1}$. HRMS (MALDI) calcd for C$_{33}$O$_{26}$O$_5$ [M+Na$^+$] 525.1672 found 525.1686.

An illustrative example of the use of 9-anthracene methanol (C) for the preparation of mixed and di-9-anthryl esters is:

1-adamantyl 9-anthrylmethylate (12, X=—O—CO—):

1-adamantyl 9-anthrylmethylate was prepared from 9-anthracene methanol (277 mgr, 1.33 mmoles) and 1-adamantane carboxylic acid (200 mgr, 1.11 mmoles), following the procedure described for the preparation of 5. Purification was succeeded by flash chromatography (yellow solid, 262 mgr, 63.7%). $^1$H (250 MHz, CDCl$_3$): δ 8.20 (3H, d), 7.80 (2H, d), 7.50-7.20 (4H, dt), 5.95 (2H, s), 1.85 (10H, s), 1.45 (5H, s); $^{13}$C NMR (62.5 MHz, CDCl$_3$): δ 177.8, 130.9, 130.3, 128.8, 126.3, 124.7, 123.4, 58.4, 40.1, 37.5, 30.6, 29.8 ppm; FTIR 3040, 2931, 2853, 1712, 1449, 1268, 1181, 1102, 952, 891, 729 cm$^{-1}$. HRMS (MALDI) calcd for C$_{26}$H$_{26}$O$_2$ [M+.] 370.1933 found 370.1946.

An illustrative example of the use of 9-anthracene methanol (C) for the preparation of di-9-anthryl methyl carbonates is:

Di-9-anthrylmethylarbonate (13, X=—O—CO—O—):

Di-9-anthrylmethyl carbonate was prepared from 9-anthracene methanol (656.3 mgr, 3.15 mmoles) and CDI (176.6 mgr, 1.09 mmoles), according to the procedure followed for the preparation of carbonate 9 (X=—O—CO—O—). The crude product was purified by flash chromatoraphy and recrystallization (green-yellow crystals, 159 mgr, 33%). $^1$H NMR (250 MHz, CDCl$_3$): δ 8.45 (2H, s), 8.45 (4H, d), 8.08 (4H, d), 7.55-7.35 (8H, m), 6.25 (4H, s) ppm; $^{13}$C NMR (62.5 MHz, CDCl$_3$): δ 155.19, 129.26, 128.89, 126.67, 124.85, 123.75, 62.22 ppm; FTIR: 3050.0, 2900.0, 1745.2, 1268.6, 1235.0, 917.6, 891.8, 727.3 cm$^{-1}$. MS (EI) m/z 442 (M$^+$).

An illustrative example of the use of 9-chloromethyl-anthracene (D) for the preparation of mixed 9-aminomethyl anthryl derivatives is:

1-(9-aminomethyl-anthryl)-adamantane (16, X=—CH$_2$—N—, R$^1$=1-adamantyl-, R$^2$=—H):

A solution of 9-chloromethyl-anthracene, (300 mgr, 1.32 mmoles), 1-adamantamine hydrochloride (298 mgr, 1.59 mmoles) and sodium carbonate (433 mgr, 3.18 mmoles) in acetonitrile was refluxed, overnight. The reaction mixture was concentrated in vacuo and the product was purified by flash chromatography (chloroform-methanol) (yellow solid, 208.3 mgr, 46%). $^1$H NMR (250 MHz, CDCl$_3$): δ 8.30 (2H, d), 8.22 (1H, s), 7.90 (2H, d), 7.38-7.30 (4H, m), 4.58 (2H, s), 2.10 (3H, s), 1.90 (6H, s), 1.65 (7H, s) ppm; $^{13}$C NMR (62.5 MHz, CDCl$_3$): δ 132.5, 131.6, 130.2, 129.1, 128.3, 127.4, 126.8, 126.7, 126.6, 125.9, 124.8, 124.6, 124.1, 51.3, 43.9, 42.8, 36.8, 36.6, 29.7 ppm; FTIR: 3048.1 2917.2, 2836.7, 1452.2, 737.4 cm$^{-1}$. HRMS (MALDI) calcd for C$_{25}$H$_{27}$N [M+Na$^+$] 342.2216, found 342.227.

Two illustrative examples of the use of 9-chloromethyl anthracene (D) for the preparation of di-9-anthrylmethyl-amino-derivatives is:

N,N-Di-(9-anthrylmethyl)-amine (16, X=—CH$_2$—N—, R$^1$=9-anthrylmethyl-, R$^2$=H—):

A solution of 9-chloromethyl anthracene (278 mgr, 1.22 mmoles) in dichloromethane (1.5 ml) was bubbled with gaseous ammonia for 10 minutes. More dichloromethane was added, the reaction vessel was tightly closed and the reaction mixture was stirred for two days, at room temperature. Concentration in vacuo and purification of the crude product by flash chromatography afforded 30 mgr (14%) of N,N-di-(9-anthrylmethyl)-amine as yellow solid. $^1$H NMR (250 MHz, CDCl$_3$): δ 8.48 (2H, s), 8.25-8.10 (4H, m), 8.09-7.80 (4H, m), 7.55-7.25 (8H, m), 4.95 (4H, s), 1.98 (NH, broad) ppm; $^{13}$C NMR (62.5 MHz, CDCl$_3$): δ 131.8, 131.3, 130.4, 129.3, 128.4, 126.2, 125.1, 124.2, 45.6 ppm; FTIR: 3317, 3052, 2919, 2846, 1938, 1726, 1620, 1448, 1096, 1030, 891, 738 cm$^{-1}$. HRMS (MALDI) calcd for C$_{30}$H$_{23}$N [M+H$^+$] 398.1903, found 398.1917.

trans-1,2-Di-9-aminomethyl-anthryl)cyclohexane (17, X=—N—, R$^1$=9-anthrylmethyl-, R$^2$=H—):

trans-1,2-Di-(9-aminomethyl-anthryl)-cyclohexane, was prepared from 9-chloromethyl anthracene (600 mgr, 2.63 mmoles) and trans-1,2-diaminocyclohexane (100 mgr, 0.88 mmoles), according to the procedure described for the preparation of compound 16 (X=CH$_2$—N—, R$^1$=9-anthrylmethyl-, R$^2$=H—). Purification by flash chromatography afforded 130.6 mgr (30%), of trans-1,2-di-(9-aminomethyl-anthryl)-cydohexane as yellow crystals. $^1$H NMR (250 MHz, CDCl$_3$): δ 8.28 (2H, s), 8.00 (2H, d), 7.81 (2H, d), 7.20-7.10 (4H, m), 7.00-6.80 (4H, m), 4.80 (2H, d), 4.30 (2H, d), 2.40 (4H, br), 1.83 (2H, br), 1.30 (4H, br) ppm; $^{13}$C NMR (62.5 MHz, CDCl$_3$): δ 131.2, 130.0, 128.8, 126.8, 125.6, 124.4, 123.4, 62.0, 42.9, 31.5, 24.6 ppm; FTIR: 3297, 3257, 3052, 2926, 2853, 2177, 1448, 1109, 871, 731 cm$^{-1}$. HRMS (MALDI) calcd for C$_{36}$H$_{34}$N$_2$ [M+H$^+$] 495.2795 found 495.2782.

Two illustrative examples for the use of 9-anthracarbaldehyde (E) for the preparation of mixed and poly-anthryl derivatives are the following:

Mixed anthryl ester (21, X=—CO—):

To a mixture of diol (20) (104.1 mgr, 0.39 mmoles), prepared according to Ishikawa (J. Ishikawa, H. Sakamoto, S. Nakao, H. Wad, *J. Ogr. Chem.* 1999, 64,1913-1921) (scheme 5) and 1-adamantane carboxylic acid (196.8 mgr, 1.09 mmoles), in dichloromethane (0.1 ml), under argon, a catalytic amount of 4-DMAP and EDC.HCl (224.4 mgr, 1.17 mmoles) were added, at ice bath temperature. The reaction mixture was heated at 40° C., overnight. Conventional workup described for the preparation of ester (5) and flash chromatography of the crude product afforded 92.7 mgr (40%) of pure yellow solid. $^1$H NMR (250 MHz, CDCl$_3$): δ 8.30 (1H, s), 8.25 (2H, d), 7.90 (2H, d), 7.42-7.22 (4H, m), 4.19-3.95 (4H, m), 3.65 (2H, d), 2.55 (1H, m) 2.10-1.80 (18H, 2 broad singlets), 1.78-1.48 (12H, br); $^{13}$C NMR (62.5 MHz, CDCl$_3$): δ 177.7, 131.2, 129.6, 128.9, 126.2, 125.8, 124.6, 123.4, 68.9, 40.8, 40.0, 38.5, 36.2, 29.4, 27.3, 25.4 ppm; FTIR: 3049.0, 2920.5, 2839.0, 1749.4, 1459.1, 1230.0, 1077.2, 731.0 cm$^{-1}$. HRMS (MALDI) calcd for C$_{40}$H$_{46}$O$_4$ [M+Na$^+$] 613.388, found 613.3311.

Penta-anthryl ester (22, X=—CO—CH$_2$CH$_2$CO—):

Penta-antryl ester (22, X=—CO—CH$_2$CH$_2$—CO—) was synthesized from diol (20) (45.18 mgr, 0.170 mmoles), acid (4) (200 mgr, 0.390 mmoles), EDC.HCl (83.14 mgr, 0.425 mmoles) and a catalytic amount of 4-DMAP, according to the procedure described for the preparation of the ester (5). The crude product was purified by flash chromatography affording 98 mgr (45.9%) of (22) as yellow solid. $^1$H NMR (250 MHz, CDCl$_3$): δ 8.27 (5H, s), 8.15-7.75 (20H, m), 7.40-7.10 (20H, m), 5.80-5.60 (2H, m), 4.30-3.80 (8H, m), 3.78-3.60 (4H, m), 3.45 (2H, d), 2.42 (9H, s) ppm; FTIR: 3063.1, 2925.5, 1731.9, 1156.7, 888.8, 731.8 cm$^{-1}$. HRMS (MALDI) calcd for C$_{88}$H$_{7OO8}$ [M+Na$^+$] 1277.4963, found 1277.4963.

Two illustrative examples of the use of 9-anthracene carboxylic add (F) for the synthesis of mono- or poly- and mixed-anthryl esters and amides are the following:

N-(n-butyl-)-9-anthrylamide (24, X=—CO—NH—, R=n-butyl-):

A solution of 9-anthracene carboxylic acid (300 mgr, 1.35 mmoles) in thionyl chloride (3.3 ml) was refluxed for 1 hour. The reaction mixture was concentrated in vacuo, dry toluene was added and the solution was concentrated in vacuo again for the complete removal of thionyl chloride. After the chloride was dissolved in toluene (1.2 ml), sodium carbonate (280 mgr, 2.03 mmoles) and 1-butylamine (148 mgr, 2.03 mmoles) were added. The reaction mixture was stirred at room temperature overnight under argon and then it was partitioned between water and ethyl acetate. The aqueous phase was washed 3 times with ethyl acetate and the combined extracts were washed with water, HCl (1N), water, brine, dried over sodium sulfate and concentrated in vacuo. The crude product was purified by flash chromatography to afford 300 mgr (80%) of yellow solid. $^1$H NMR (250 MHz, CD$_3$OD): δ 8.65 (1H, s), 8.15-8.01 (4H, m), 7.64-7.50 (4H, m), 3.66 (2H, t), 2.20 (NH, s), 1.86-1.72 (2H, m), 1.66-1.49 (2H, m), 1.09 (3H, t) ppm; FTIR: 3230.6, 3050.0, 2950.6, 2870.0, 2378.0, 1610.2, 1572.0, 1253.9, 740.9 cm-1. HRMS (MALDI) calcd for C$_{19}$H$_{19}$NO [M+H$^+$] 278.1539, found 278.1531 cm$^{-1}$.

5-pregnen-3β-yl-(9-anthryl-methylate)-20-one (25, X=—CO—):

5-pregnen-3β-yl-(9-anthryl-methylate)-20-one (25, X=—CO—) was synthesized by 9-anthroyl chloride (100 mgr, 0.45 mmoles), 5-pregnen-3β-ol-20-one (185.14 mgr, 0.58 mmoles) and sodium carbonate (81 mgr, 0.60 mmoles), following the previous procedure. The crude product was purified by flash chromatography yielding 159.3 mgr (68%) of a pale yellow solid. $^1$H NMR (250 MHz, CDCl$_3$): δ 8.50 (1-H, s), 8.08 (4H, m), 7.65-7.42 (4H, m), 5.55 (1H, br), 5.4-5.18 (1H, m), 2.8-2.45 (4H, m), 2.25-1.95 (10H, m), 1.90-1.42 (9H, m), 1.40-1.00 (6H, m) ppm; $^{13}$C NMR (62.5 MHz, CDCl$_3$): δ 209.5, 185.0, 145.4, 139.4, 131.0, 129.1, 128.6, 128.6, 128.2, 126.9, 126.9, 125.4, 124.9, 122.8, 75.5, 63.6, 56.8, 49.9, 44.0, 38.8, 38.2, 37.1, 36.7, 31.8, 31.5, 28.0, 24.5, 22.8, 21.0, 19.3, 13.2 ppm; FTIR: 3050.0, 2990.4, 2936.5, 1717.7, 1698.1, 1357.3, 1204.4, 1000.2, 731.6 cm$^{-1}$. MS (EI) m/z 520 (M$^+$).

3. Detailed Description of the Physicochemical Characterization and Use of Synthesized Compounds as Resist Additives The improvement of selected physicochemical properties, defining the behavior of the additives was tested, with the help of standard lithographic resist materials. PMMA was mostly used since it is a common, simple and well-known material and thus it can provide a universal matrix for the evaluation of the proposed additives. It has also low absorbance at 193 nm and it is characterized by low etch resistance (Ohnishi number O=5, Ring Parameter R=0). This way, the improvement obtained by loading the resist film with the synthesized additives can be easily assessed. For comparison purposes, simple anthracene derivatives were first tested. Anthracene was the basic structure initially studied. The effect of several simple derivatives on UV absorbance, solubility, sublimation and etch resistance of the common aliphatic resist PMMA was evaluated. The commercially available anthracene, 9-anthracene methanol, 9-anthracene carboxylic acid and 2-aminoanthracene were first tested and considered as reference compounds. Consequently, newly synthesized compounds containing other functional groups and either two or more anthryl-moieties or one or more anthryl groups linked to polycarbocycles, such as adamantane, steroids etc., were also tested and compared to known di- and poly-anthryl-derivatives. A commercial broadband UV photoresist AZ5214, and an experimental 193 nm acrylate-based photoresist with improved etch resistance compared to PMMA were also tested. Both Reactive ion Etching (RIE) and Inductively Coupled High Density plasma reactors were used. Although most of the results are in Oxygen plasmas, Fluorine and Chlorine containing plasmas were also tested.

It is important that the selected additive is soluble in the solvents commonly used in the microlithography process. In the cases where Poly(methyl methacrylate) (PMMA), was used as the base polymer, Propylene Glycol Methyl Ether Acetate (PGMEA) and Methyl Isobutyl Ketone (MIBK) were used as solvents. After film formation the amount of the additive sublimed during the baking cycles was tested. Evaluation of spectroscopic and etch resistance enhancement followed.

Examples of physicochemical and lithographic evaluation procedures in resist formulations are described in the following examples:

Example 1

A solution of poly (methyl methacrylate) (PMMA), of 8% w/w in methyl isobutyl ketone (MIBK), was prepared. A quantity of a polyaromatic compound (i.e.compound (XI), Table 9), was added in part of this solution at a 7.5% w/w of the polymer concentration.

The solution was stirred at room temperature for a few hours and the polyaromatic compound was dissolved. Then, a small amount of the solution was used to spin coat a film on quartz substrate at 4000 rpm for 30 sec. The thickness of this film was measured by a profilometer and found 12250 Å. The absorption spectrum of the film was taken at vertical incidence.

The same procedure was repeated, using the initial PMMA solution this time. A new film was spun and its thickness was found 13000 Å.

Normalizing each of the above films thickness at 5000 Å it was calculated that the excess absorption induced by the addition of the polyaromatic compound in PMMA was 0.05 per 0.5 μm thickness of the film, at the region of 193 nm wavelength.

After this step, films were heated on a hotplate at 90° C. for 5 min and the absorption spectra were taken again. The same procedure was repeated for heating at 110° C., 130° C. and 160° C. The spectra taken each time were compared and the possible sublimation of the additive after the different thermal treatment procedures was calculated. The results are shown in Tables 5-9.

Example 2

On a 3" Si wafer a thin film from a PMMA solution was spin coated, as it was described in example 1. On another substrate, a PMMA film containing the additive under testing was spin coated.

Both samples were post-applied bake on a hotplate at 110° C. for 5 min. Thickness was measured and then the films were etched in $O_2$ plasma, introducing them one after the other in the center of the chamber in a Reactive Ion Etcher. The etching conditions were the following: $O_2$ flux 50 sccm, pressure 10 mTorr, RF power 400 W (electrode diameter 300 mm), DC bias 150V, and time of etching 120 sec (2 min). After etching the film thickness was measured again. Dividing the thickness differences with etching time the etching rates were obtained. Results are presented in table 1, where a 21% decrease of the etching rate of PMMA film due to the addition of the polyaromatic compound is evident.

TABLE 1

Etching rates of PMMA films in Oxygen plasma

| Material | Thickness before etching (Å) | Thickness after etching (Å) | Thickness differences (Å) | Etching rates (Å/min) |
| --- | --- | --- | --- | --- |
| PMMA | 11.900 | 5.300 | 6.600 | 3.300 |
| PMMA loaded with compound (XI) (table 9) | 9.800 | 4.600 | 5.200 | 2.600 |

Example 3

Four wafers were prepared as in examples 1 and 2. The wafers were etched in an inductively coupled high density plasma reactor with the following conditions: top ICP power 600 W, bias voltage 100V, pressure 10 mTorr, electrode temperature 15° C., gas flow 100 sccm. Two wafers were etched in Oxygen plasma (one with the additive and the other without additive), and two wafers were etched in Sulfur Hexafluoride ($SF_6$) plasma. Table 2 shows the etch-resistance improvement in the two plasmas used in the ICP reactor.

TABLE 2

Etching rates for PMMA films in High Density Plasma ($O_2$ or $SF_6$)

| Material | Etching Rates in $O_2$ Plasma (Å/min) | Etching Rates in $SF_6$ Plasma (Å/min) |
| --- | --- | --- |
| PMMA | 4300 | 2770 |
| PMMA loaded with compound (XI), (table 9) | 3600 | 2410 |

Example 4

Films were spin coated from solutions described in example 2. As substrates, very careful cleaned Si wafers (dipped into a $H_2SO_4$:$H_2O$ 1:1 solution and then into a HF solution and heated at 160° C. for 15 min) were used and priming was applied in each wafer for better adhesion of the films.

After spin coating films were heated on a hotplate at 95° C. for 15 min and patterned by illumination with a mask-aligner through a photo-mask for 25 sec. A TMAH 0.27 N solution was used for the development (3.5 min). Inspection under the optical microscope revealed capability for the formation of submicron structures, and no visible alteration of the imaging properties of AZ 5214.

Example 5

PMMA solution 8% w/w in PGMEA was prepared. In one part of the solution 9-anthracene methanol (5% w/w of the polymer) was added. Films from both solutions were spin coated, as in example 1, and heated on a hotplate at 90° C. for 5 min. Film thickness was found 7700 Å and 7800 Å, respectively.

Then, films were broadband exposed using a 500 W Hg—Xe exposure tool through a lithographic mask for various doses and developed in a MIBK(methyl-isobutyl—ketone):IPA (isopropyl alcohol) 1:1 solution for 2 min. Finally, films were rinsed with IPA and dried in a $N_2$ flow.

The exposed areas were dissolved in different degrees depending on the doses, which means that the films show positive lithographic behavior. Results are shown in Table 3.

TABLE 3

Lithographic behavior of PMMA films.

| Exposure time (sec) | Remaining thickness PMMA (Å). | Remaining thickness PMMA loaded with 9-anthracene methanol (Å) |
| --- | --- | --- |
| 1000 | 5500 | 6300 |
| 1200 | 4900 | 5700 |
| 1400 | 1600 | 5400 |
| 1600 | 1200 | 5200 |
| 1800 | 900 | 3200 |
| 2000 | 0 | 1600 |
| 2400 | 0 | 500 |
| 2800 | 0 | 0 |
| 3000 | 0 | 0 |

Example 6

An experimental acrylate-based 193 nm photoresist with improved etch resistance compared to PMMA (Ohnishi number O=4.64, Ring Parameter R=0.129—compared with O=5 and R=0 of PMMA) was tested in an Inductively Couple Plasma Reactor with a standard Polysilicon etching recipe ($Cl_2$/HBr chemistry). One wafer was coated with the experimental resist, while another was coated from a solution containing the photoresist and 10% additive XI see table 9. Table 4 shows the results of etching for one minute. A large reduction of the etching rate of the experimental resist is seen.

TABLE 4

Standard polysilicon etch data

| Resist Formulations | Initial Film Thickness (nm) | Film Thickness upon Etching (nm) | Film Thickness Loss (1 min) (nm) | % Film Thickness Loss |
|---|---|---|---|---|
| Experimental acrylate without additive | 320 | 220 | 100 | 31.25 |
| Experimental acrylate with 10% additive XI see table 9 | 342 | 290 | 52 | 15.20 |

Example 7

An experimental 193 nm acrylate-based photoresist (the same as in example 6) was used in two versions. One with 10% additive XI (see table 9), and the other without additive. The two resist versions had different Photo-acid generator concentrations to ensure equal absorbances. Exposures were done with a 193 nm scanner for high resolution imaging (0.100-0.20 μm). Comparison of the lithographic results of the two resist versions (with/without additive) showed no loss of resolution capability or imaging quality. Small shifts in sensitivity and development time were only observed. This demonstrated that the proposed additive could be used in photoresists for high-resolution imaging and high etching resistance.

Characteristic results obtained from the different evaluation experiments are presented in the following Tables 5-9. The following explanations apply to all tables. UV=absorbance at 193 nm or at 248 nm/0.5 μm. SOL=solubility at the solvents used (##=very bad, #=bad, *=good, **=very good). SUBL=temperature of sublimation. ETCH RATE=Oxygen plasma etching rate in Å/min) with additive present in PMMA in 7.5% w/w of the polymer, except from Table 5 where additives are present at 5% w/w of the polymer. (Conditions: RIE mode, 10 mTorr, 400 W power, electrode diameter 300 mm, DC bias 150V, etching time 2 min. Etching rate of pure PMMA is 3300 Å/min. nt=not tested, O.N.=Ohnishi number (the smaller the better the etch resistance) and R.P.=Ring parameter (the higher and closer to unity the better the etch resistance). O.N.(PMMA)=5, O.N.(PHS poly hydroxy styrene)=2.43, R.P.(PMMA)=0, R.P.(PHS)=0.6

TABLE 5

Reference mono- anthryl derivatives and their physicochemical properties.

| REFERENCE COMPOUNDS | UV 193 nm | SOL | SUBL | ETCH RATE | O.N | R.P. |
|---|---|---|---|---|---|---|
| 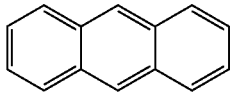 | 0.38 | * | 110° C. | 3017 | 2.40 | 0.94 |
| 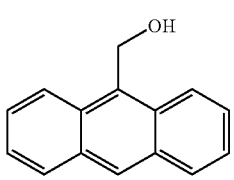 | 0.43 | * | 110° C. | 3017 | 2.00 | 0.81 |
| 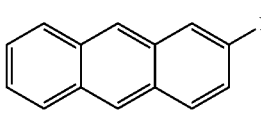 | 0.51 | * | 110° C. | 2435 | 1.86 | 0.87 |
| 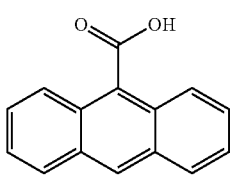 | 0.46 | * | 110° C. | 3017 | 2.08 | 0.76 |

Note: absorbance values in this table (only) include the PMMA absorbance (are higher by 0.07). They also refer to 5% of additive w/w with respect to the polymer, rather than 7.5% of all other following tables.

TABLE 6
Known di-anthryl derivatives and their physicochemical properties
| KNOWN DI-DERIVATIVES | UV 193 nm | UV 248 nm | SOL | SUBL | ETCH RATE | O.N. | R.P. |
|---|---|---|---|---|---|---|---|
| 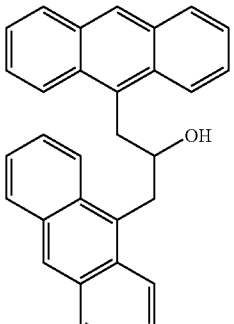<br>(I) | 0.16 | 0.48 | ** | 160° C. | 2700 | 1.87 | 0.82 |
| 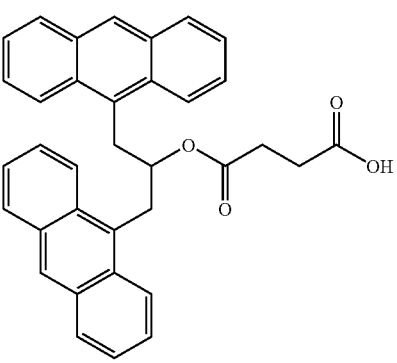<br>(II) | 0.33 | 1.25 | ** | 160° C. | 2850 | 2.16 | 0.66 |
| 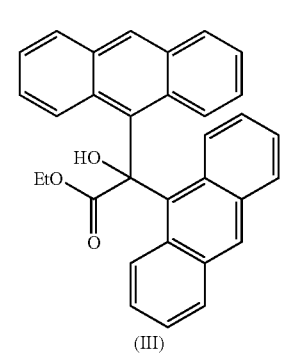<br>(III) | 0.42 | 0.67 | ** | 110° C. (reacts) | 3393 | 2.03 | 0.74 |

TABLE 6-continued

Known di-anthryl derivatives and their physicochemical properties

| KNOWN DI-DERIVATIVES | UV 193 nm | UV 248 nm | SOL | SUBL | ETCH RATE | O.N. | R.P. |
|---|---|---|---|---|---|---|---|
| (IV) | 0.22 | 0.31 | * | 160° C. | nt | 1.80 | 0.85 |

TABLE 7

Novel di-anthryl derivatives and their derivatives and their physiochemical properties

| NOVEL DI-DERIVATIVES | UV 193 nm | UV 248 nm | SOL | SUBL | ETCH RATE | O.N. | R.P. |
|---|---|---|---|---|---|---|---|
| (V) | 0.29 | 0.63 | ## | 130° C. | nt | 2.00 | 0.76 |
| (VI) | 0.24 | 1.04 | * | 130° C. | 3067 | 2.28 | 0.67 |

TABLE 7-continued

Novel di-anthryl derivatives and their derivatives and their physiochemical properties

| NOVEL DI-DERIVATIVES | UV 193 nm | UV 248 nm | SOL | SUBL | ETCH RATE | O.N. | R.P. |
|---|---|---|---|---|---|---|---|
| (VIII) | 0.35 | 1.16 | # | 160° C. | 2800 | 1.86 | 0.82 |
| (VII) | 0.10 | 0.40 | ** | 160° C. | 2900 | 2.00 | 0.83 |

TABLE 8

Known and novel poly-anthryl derivatives and their physichocemical properties

| KNOWN POLY DERIVATIVES | UV 193 nm | UV 248 nm | SOL | SUBL | ETCH RATE | O.N. | R.P. |
|---|---|---|---|---|---|---|---|
| (IX) | 1.41 | 1.74 | # | 160° C. | 2850 | 2.00 | 0.72 |

TABLE 8-continued

Known and novel poly-anthryl derivatives and their physichocemical properties

| NOVEL POLY DERIVATIVES | UV 193 nm | UV 248 nm | SOL | SUBL | ETCH RATE | O.N. | R.P. |
|---|---|---|---|---|---|---|---|
| (X) | 0.33 | 0.75 | # | 160° C. | 2750 | 1.89 | 0.67 |

TABLE 9

Novel mixed anthryl derivatives and their physicochemical properties

| NOVEL MIXED DERIVATIVES | UV 193 nm | UV 248 nm | SOL | SUBL | ETCH RATE | O.N. | R.P. |
|---|---|---|---|---|---|---|---|
| (XI) | 0.05 | 0.36 | ** | 160° C. | 2600 | 2.25 | 0.78 |
| (XII) | 0.26 | 0.86 | ** | 130° C. | 2800 | 2.08 | 0.88 |

TABLE 9-continued

Novel mixed anthryl derivatives and their physicochemical properties

| NOVEL MIXED DERIVATIVES | UV 193 nm | UV 248 nm | SOL | SUBL | ETCH RATE | O.N. | R.P. |
|---|---|---|---|---|---|---|---|
| (XIII) | 0.17 | 0.45 | ** | 160° C. | 3100 | 2.50 | 0.69 |
| (XIV) | 0.20 | 0.52 | * | 160° C. | 2700 | 2.39 | 0.72 |

As it is concluded from the results of Tables 5-9, this new generation of anthryl derivatives has much better physicochemical properties than any reported compound, so far (reference compounds, Table 5). In particular, when the anthryl groups were tethered via an ester group the etch resistance as well as the temperature of sublimation were significantly enhanced, without any dramatic effect on UV absorbance. However, the solubility was not satisfactory in certain cases e.g. compound (VII). The presence of carbonates in di-anthryl derivatives resulted in less improvement in the temperature of sublimation e.g. compounds (V) and (VI). Tethering the anthryl groups via a carbon skeleton—containing either hydroxyl, or ester groups (e.g. compounds (I) and (II)), or a substituted amino group (e.g. compound (VIII))—resulted not only in a significant increase in the temperature of sublimation, and etch resistance, but also in improved solubility.

There seemed to be a limit in etch resistance enhancement with the increase of the anthryl groups per molecule, while the presence of many anthryl groups in the same compound resulted in decreased solubility e.g. compounds (IX) and (X), (Table 8). The limit in etch resistance with the increase of the anthryl groups is evidenced by the deterioration of the Ohnishi and Ring Parameters (e.g. (I) and (IX) tables 6 and 8, respectively).

Additives containing at least one adamantane or steroid along with the anthracene are characterized as mixed. These additives were also tested in PMMA, and an experimental 193 nm photoresist as described in examples 1, 2, 3, 6 and 7 and the results are shown in Table 9 for PMMA. Generally, the presence of adamantane or steroid resulted in a significant improvement of absorbance. In particular, the very simple mixed derivative (XI), combined excellent plasma etch resistance with very good solubility, high temperature of sublimation and small UV absorbance.

These additives can, in principle, be used for any photoresist requiring etch resistance enhancement. Moreover, these additives have the potential to be used in novel applications where enhanced etch resistance is required. However, the requirement is that the Ohnishi number of the additives is lower compared to the original photoresist, or in other terms, the Ring Parameter of the additive is higher compared to the ring parameter of the original photoresist. The higher the difference in Ohnishi or Ring Parameters the higher the degree of etch resistance enhancement. In cases where cycloaddition reaction happens, see Scheme 7 below, the Ohnishi or Ring parameters of the cycloaddition product should be taken into account rather than those of the initial additive.

Scheme 7: Cycloaddition reactions of anthracene derivatives under extreme UV or temperature conditions.

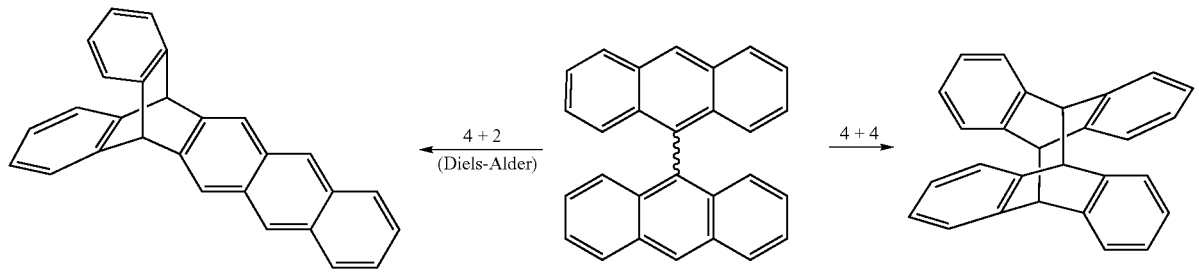

The advantages the synthesized compounds provide as resist property modifiers and in particular as etch resistance enhancement additives and as absorption modifiers are the following:

First, sublimation is substantially reduced compared to additives with only one polycarbocycle moiety. Additives that can withstand decomposition and sublimation at temperatures at least up to 160° C. can be selected from this family.

Second, etch resistance enhancement is substantial, at relatively low loading to resists having low etch resistance.

Third, absorption characteristics can be tuned by selecting suitable polycarbocyclic and functional groups.

Fourth, compatibility with common resist materials can be achieved by selecting suitable composition and functionalization.

Fifth, many compounds of the above family are especially suitable for use in 193 nm resists keeping tolerable absorbances at loading of 5-10% and provide substantial etch resistance enhancement.

In summary,
1) easy, reliable and versatile synthetic routes are provided for the facile synthesis of novel di-, poly- and mixed anthryl derivatives with desired polycarbocycle composition and tunable functionality,
2) anthryl derivatives with significantly improved physicochemical properties compared to those of simple anthracene and commercially available anthryl derivatives are also provided and
3) the use of the novel designed compounds as etch resistance enhancement and absorbance modification additives is demonstrated.

Method 6
Preparation of mono-, poly- or mixed amido-or ester derivatives 24-26, starting from 9-anthracene carboxylic acid (F) with or without a linker in accordance with the following scheme:
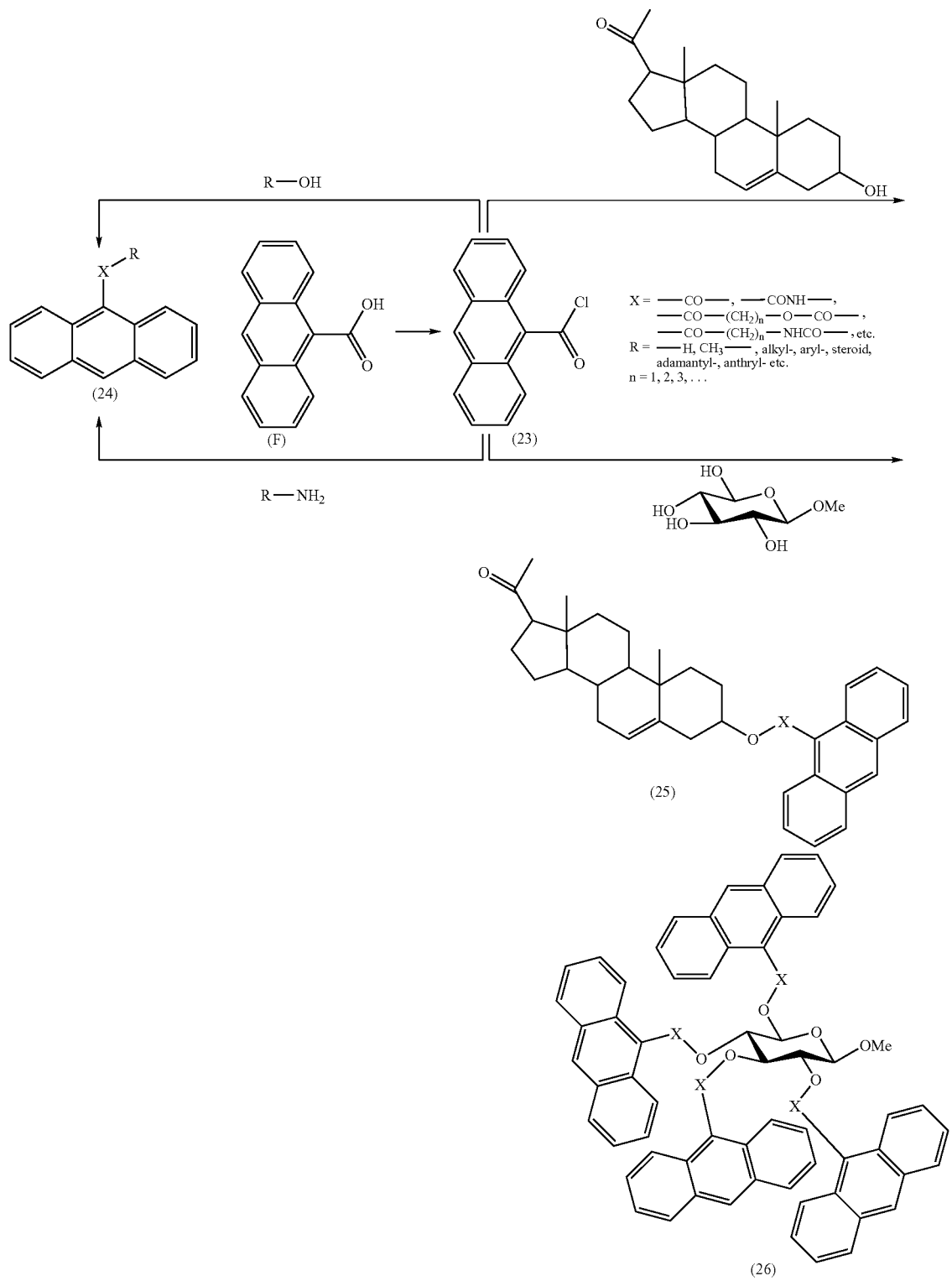

The invention claimed is:

1. A resist composition characterized in that it comprises a polycyclic compound having one of the general formulae I, II, III, IV and V,

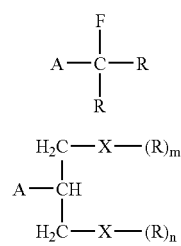

I

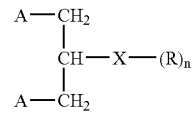

II

III

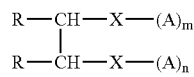

IV

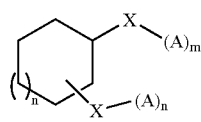

V wherein: n and m are integers of 1 to 5,

F is selected from a hydrogen atom, —OH, —NH, —COOH, alkyl or alkoxy;

X represents a linker selected from —CH$_2$—, —O—, —CH$_2$NH—, —CH$_2$O—, —CO—, NH—, —CONH—, —COO—, ALKYL, —OCOO—, —OCONH—, an oxygenated aliphatic chain, a carbonylated aliphatic chain, a carbocyclic, polysubstituted aliphatic chain and a carbocyclic with functional groups F; and A represents an anthracene or adamantane or steroid moiety of the following structures:

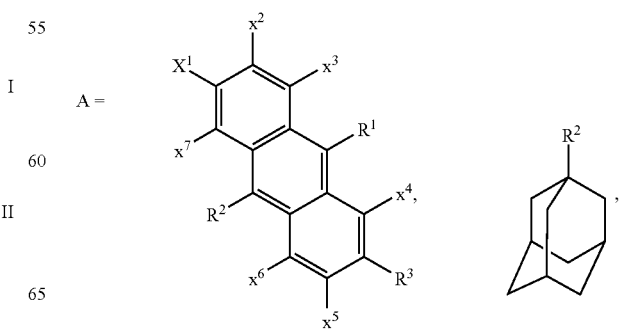

-continued

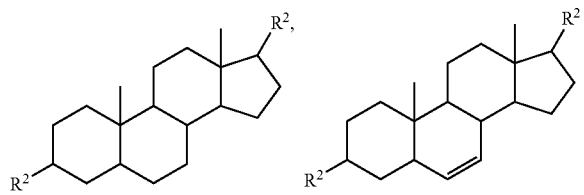

wherein:
- $R^1$ represents a hydrogen atom or alkyl or alkoxy or —(CH?)$_v$—NHCO—$R^4$ in which v is an integer of 0 to 5 and $R^4$ a hydrogen atom, alkyl or alkoxy;
- $R^2$ represents a linker selected from —CH$_2$—, —O—, —CH$_2$NH—, —CH$_2$O—, —CO—, —NH—, —CONH—, —COO—, alkyl, —OCOO—, —OCONH— and it is not connected to $R^1$ by any chain;
- $R_3$ is a functional group or a hydrogen atom;
- $X^1$ to $X^7$ may be the same as or different from one another and each thereof represents a hydrogen atom, an alkyl group, a halogen or a nitro group; and
- R represents a hydrogen atom, an alkyl group or an additional moiety of the type A, F or X defined above to provide a polycyclic compound having at least two A groups.

2. A resist composition as claimed in claim 1 in which the polycyclic compound comprises at least one anthracene moiety.

3. A resist composition as claimed in claim 1 in which the polycyclic compound is present as an etch resistance additive.

4. A resist composition as claimed in claim 1 in which the polycyclic compound is present as an absorber.

5. A resist composition as claimed in claim 1 in which $R^3$ is selected from a hydrogen atom, a halogen, an alkyl group, an alkoxy group, an amino-derivative, and a nitro group.

6. The preparation of an anthracene derivative by one of the following methods:

Method 1

Addition of the anion of anthracene, (A) derived from 9-bromoanthracene (A) and 1 equivalent of n-butyllithium, to aldehydes, ketones, epoxides, epichloridrine, and esters for the formation of mono- or d-anthryl derivatives followed by further derivatization of the above prepared alcohols of the general type 3 with several linkers to form di-or tri-anthryl derivativess of the general type 4 and 5 or mixed anthracene derivatives with adarnantane and steroids, of the general type 6 or 7, in accordance with the following scheme:

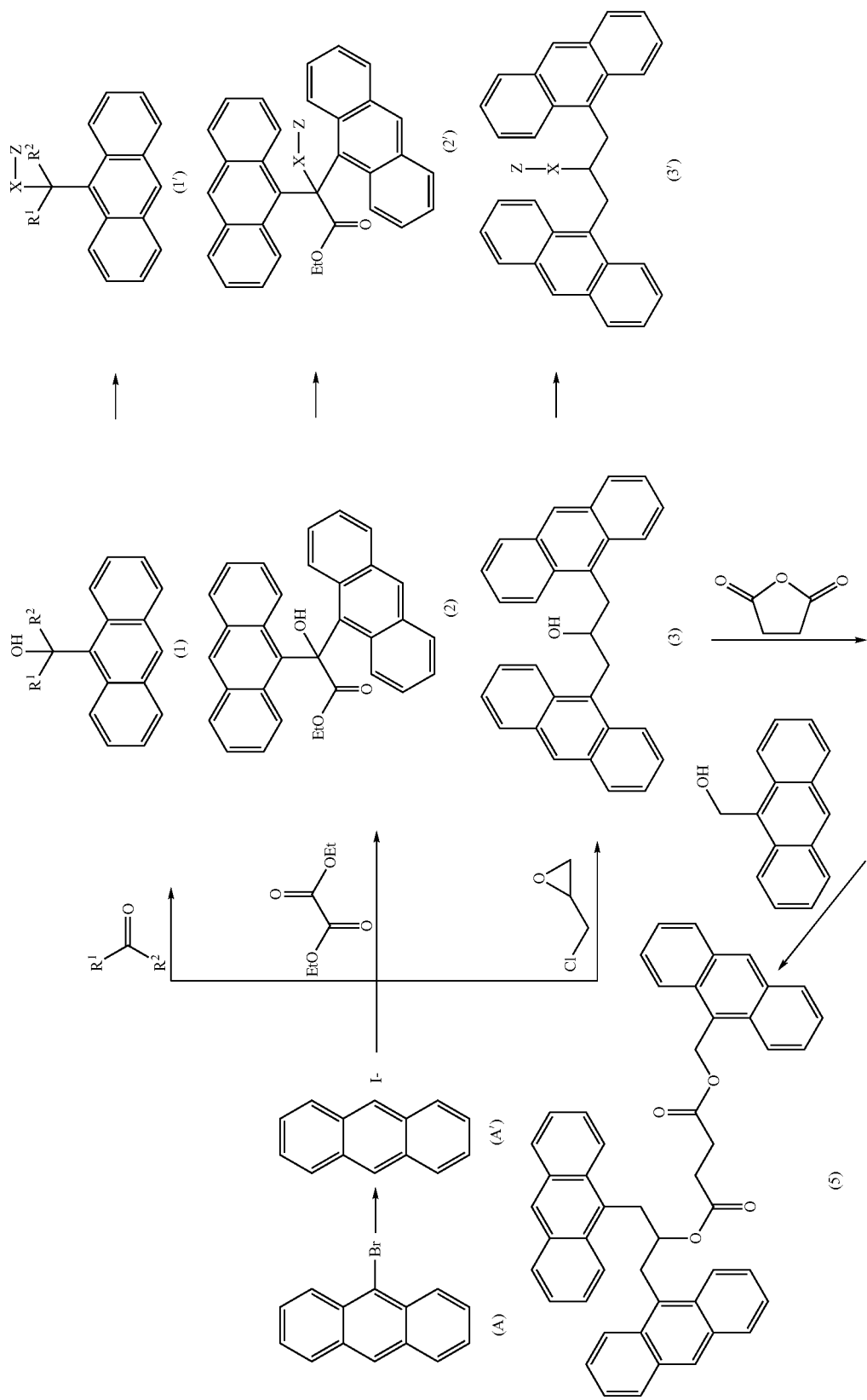

-continued
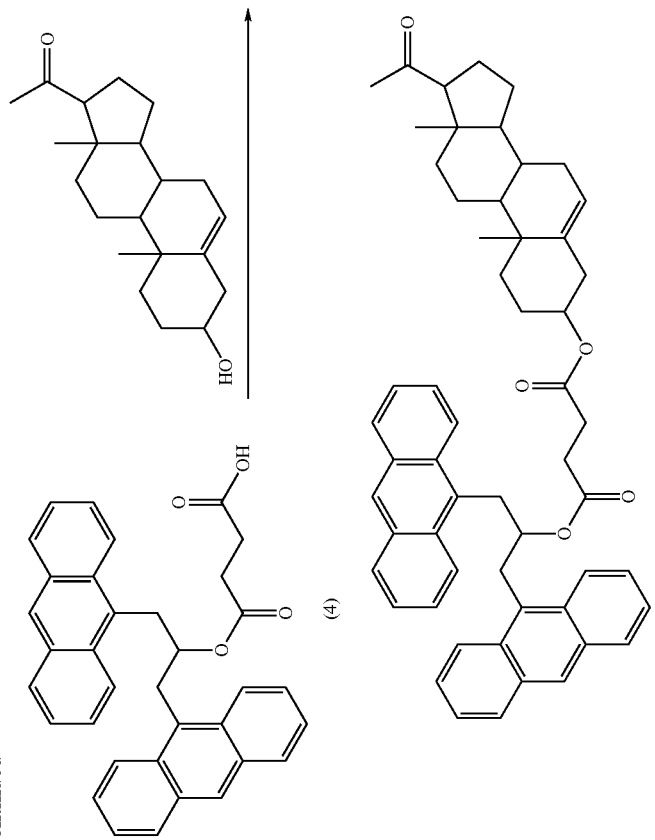
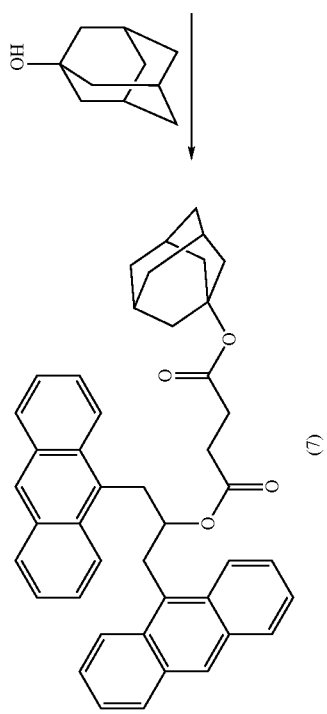
$R^1, R^2 =$ H——, alkyl-, cycloalkyl-, hydroxyalkyl-, anthryl-, adamantyl-, steriod moiety e.t.c.
$X =$ ——O——, ——O——$(CH_2)_n$——, ——O——$(CH_2)_n$——O——$(CH_2)_n$——, ——O——$(CH_2)_n$——NH——$(CH_2)_n$——, ——O——$(CH_2)_n$——CO——$(CH_2)_n$——, ——O——$(CH_2)_n$——CONH——$(CH_2)_n$——, ——O——$(CH_2)_n$——O——$(CH_2)_n$——COO—— e.t.c.
$Z =$ ——H, 9-anthryl, adamantyl, steriod moiety, cycloalkyl, e.t.c.
$n = 1, 2, 3 \ldots$ Method 2
Reaction of 9-anthrone (B) with diols and further derivatization of the resulted alcohols using linkers, to form mono-, di-, poly- and mixed anthryl derivatives of the general type 8, 9, 10 and 11 in accordance with the following scheme:

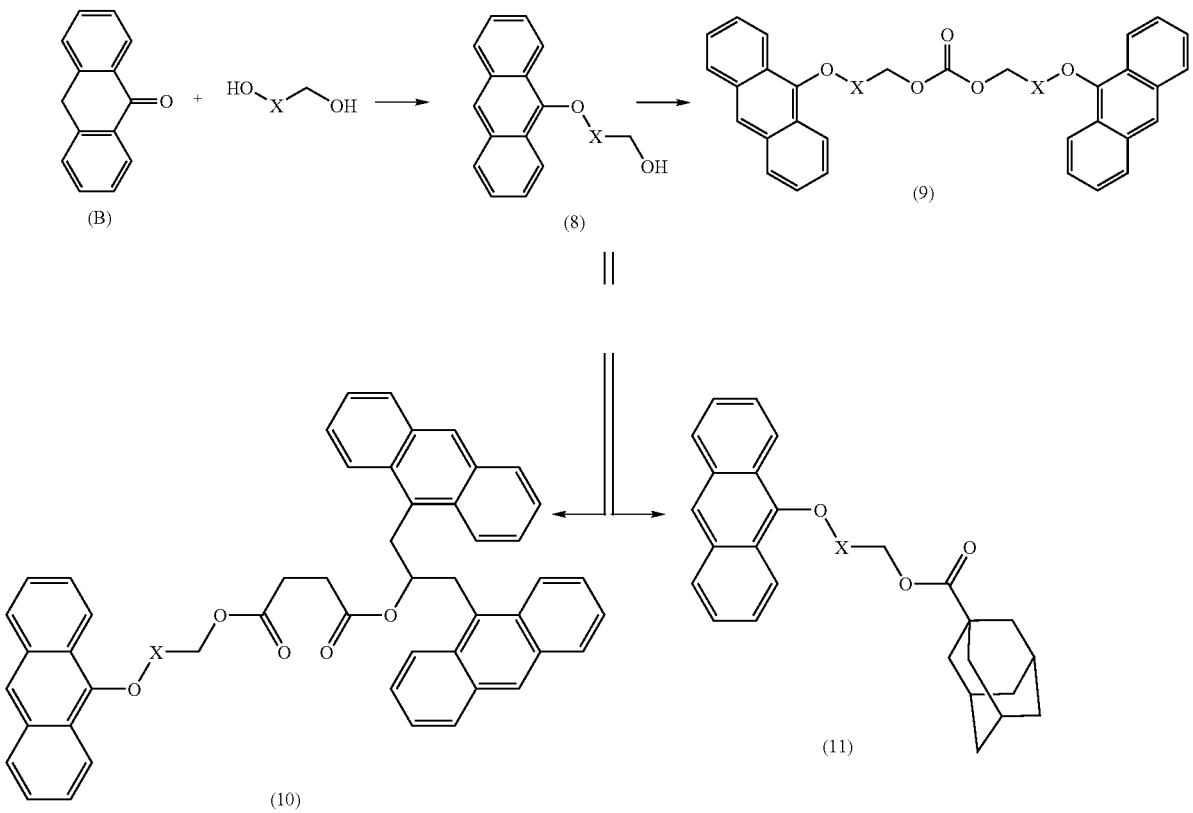

$X = -(CH_2)_n-, \ -(CH_2)_n-O-, \ -(CH_2O)_n-, \ -(CH_2)_n-NH-, \ -(CH_2)_n-CONH-, \ -(CH_2)_n-OCONH-$, etc.
$n = 1, 2, 3, \ldots$ Method 3
Derivatization of 9-anthracene methanol (C) with a linker, via esterification or etherification or amidation to form mono-, poly- or mixed derivatives of the general types 12-15 in accordance with the following scheme:

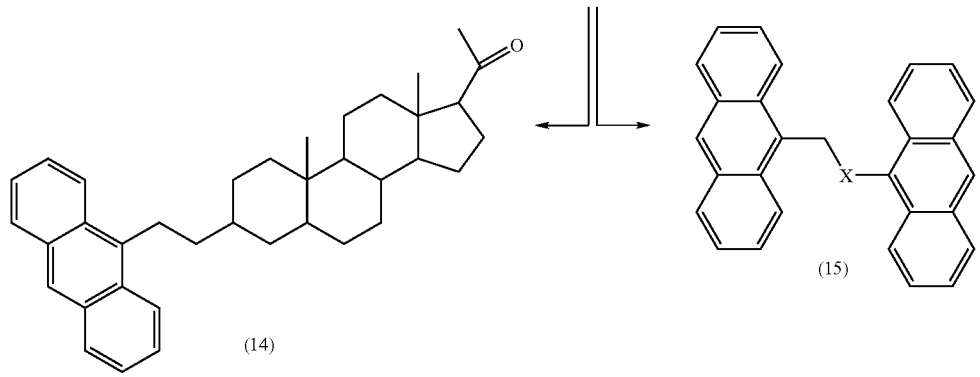

X= —O—, —O—(CH₂)ₙ—, —O—(CH₂O)ₙ—O—, —O—CO—O—, —O—CO—, —O—(CH₂)ₙ—CO—O—,
—O—CO—(CH₂)ₙ—O—, —O—CO—(CH₂)ₙ—CO—O—, —O—(CH₂)ₙ—CONH—(CH₂)ₙ—O, etc.
n = 1, 2, 3, …

Method 4

Preparation of 9-aminomethyl derivatives from 9-chloromethy anthracene (D) and primary mono-, di- or tri-amines with or without a linker, to form compounds of the general types 16-18 in accordance with the following scheme:

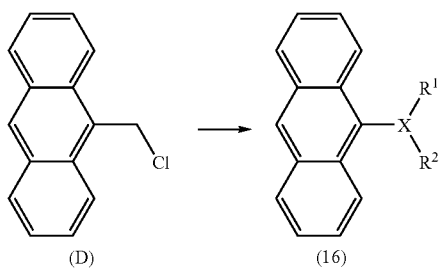

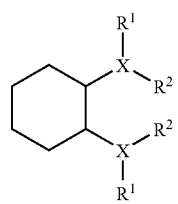

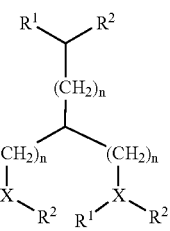

X = —(CH₂)ₙ—N—, —N—
R¹, R² = —H, —(CH₂)ₙ—OH, —(CH)ₙ—OCH₃,
—(CH₂O)ₙ—CH₃, 9-anthrylmethyl-, adamantyl- etc.
n = 1, 2, 3, …

Method 5

Preparation of mixed or poly-anthryl derivatives, of the general form 21 and 22, starting from diol 20, which is synthesized from 9-anthracarbaldehyde (E) with or without linkers in accordance with the following scheme:

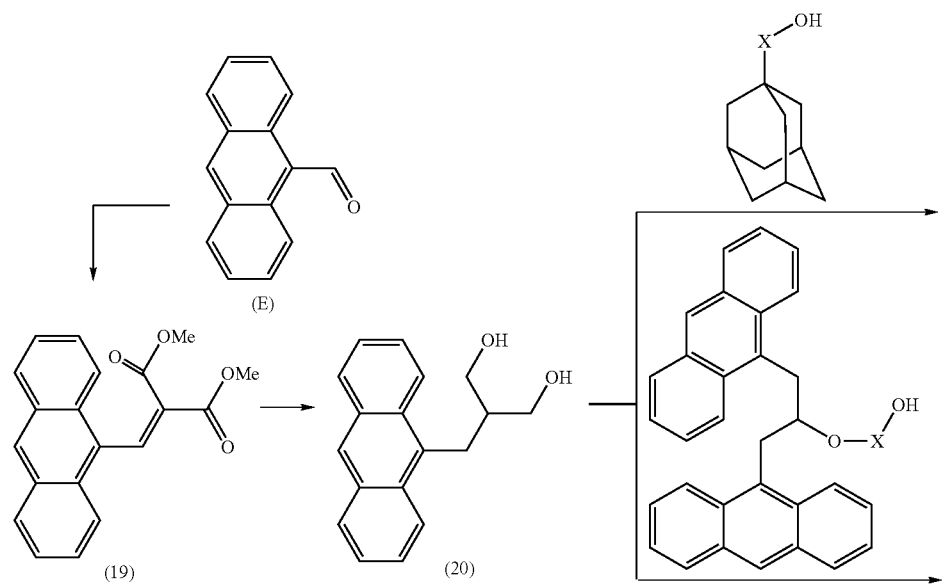
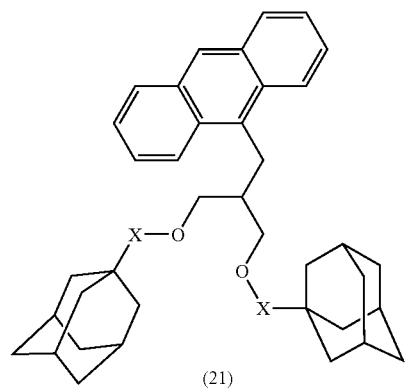
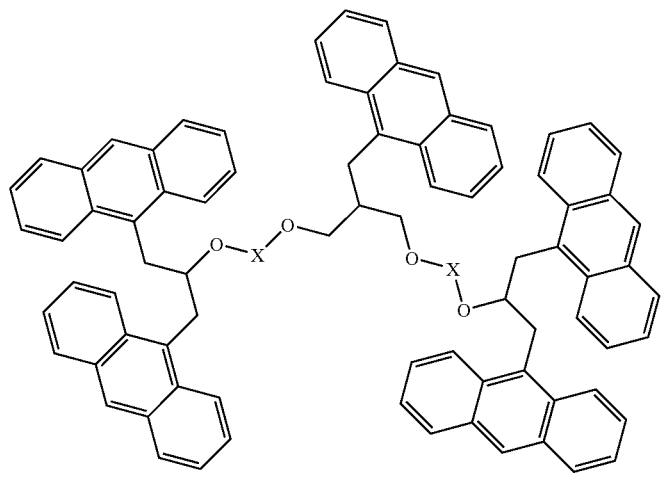
X = —(CH$_2$)$_n$—, —(CH$_2$)$_n$—O—(CH$_2$)$_n$—, —CO—, —CO—(CH$_2$)$_n$—, —(CH$_2$)$_n$—CO—(CH$_2$)$_n$—, —(CH$_2$)$_n$—CONH—(CH$_2$)$_n$—, —CO—(CH$_2$)$_n$—CO—, —(CH$_2$)$_n$—NH—(CH$_2$)$_n$—, etc.
n = 1, 2, 3, …